US008252520B2

(12) United States Patent
Lee et al.

(10) Patent No.: US 8,252,520 B2
(45) Date of Patent: Aug. 28, 2012

(54) METHODS AND COMPOUNDS FOR INHIBITING HEC1 ACTIVITY FOR THE TREATMENT OF PROLIFERATIVE DISEASES

(75) Inventors: Wen-Hwa Lee, Newport Coast, CA (US); Phang-Lang Chen, Irvine, CA (US); Yumay Chen, San Antonio, TX (US)

(73) Assignee: Taivex Therapeutics Corporation, Taipei (TW)

( * ) Notice: Subject to any disclaimer, the term of this patent is extended or adjusted under 35 U.S.C. 154(b) by 1275 days.

(21) Appl. No.: 10/530,274

(22) PCT Filed: Oct. 14, 2003

(86) PCT No.: PCT/US03/32520
§ 371 (c)(1),
(2), (4) Date: Dec. 6, 2005

(87) PCT Pub. No.: WO2004/033666
PCT Pub. Date: Apr. 22, 2004

(65) Prior Publication Data
US 2006/0140956 A1 Jun. 29, 2006

Related U.S. Application Data

(60) Provisional application No. 60/418,189, filed on Oct. 11, 2002.

(51) Int. Cl.
*A61K 31/13* (2006.01)
*A61K 31/135* (2006.01)
*A61K 31/121* (2006.01)
*A61K 31/16* (2006.01)
*A61K 31/165* (2006.01)
*A61K 31/33* (2006.01)
*C12Q 3/00* (2006.01)
*G01N 33/53* (2006.01)

(52) U.S. Cl. ............. 435/4; 435/7.1; 514/183; 514/476; 514/579; 514/617; 514/625; 514/627; 514/630; 514/646; 514/676; 514/678; 514/679; 514/685; 514/741

(58) Field of Classification Search .................. None
See application file for complete search history.

(56) References Cited

U.S. PATENT DOCUMENTS

| 4,046,878 A * | 9/1977 | Patelli et al. ............... 514/34 |
| 5,112,867 A * | 5/1992 | Kinoshita et al. ............ 514/617 |
| 5,342,947 A * | 8/1994 | Lackey et al. ................ 546/41 |
| 5,516,775 A * | 5/1996 | Zimmermann et al. ... 514/224.2 |
| 6,037,340 A * | 3/2000 | Castelhano et al. .......... 506/15 |
| 6,476,193 B1 | 11/2002 | Nandabalan et al. |
| 6,596,848 B1 | 7/2003 | Hunter et al. |
| 6,613,531 B2 * | 9/2003 | Burgess et al. ............. 435/7.1 |
| 2002/0182656 A1 | 12/2002 | Bird et al. |
| 2003/0207883 A1* | 11/2003 | Renhowe et al. ............. 514/243 |
| 2004/0077697 A1* | 4/2004 | Koshio et al. ................ 514/370 |

FOREIGN PATENT DOCUMENTS

| WO | WO98/45433 | * 10/1998 |
| WO | WO99/18856 | * 4/1999 |
| WO | WO0240717 | * 5/2002 |
| WO | WO02/062775 | * 8/2002 |
| WO | WO03/050281 | * 6/2003 |

OTHER PUBLICATIONS

Sierra and de la Torre, Angewandte Chemie, 2000, vol. 39, pp. 1538-1559.*
ChemDB, p. 1 of 3 only, downloaded from the Web on Feb. 9, 2009.*
Drug Facts and Comparisons, 1999 Edition.*
Chen, Y., et al., "Phosphorylation of the Mitotic Regulator Protein HEC1 by NEK2 Kinase is Essential for Faithful Chromosome Segregation", The Journal of Biological Chemistry, Dec. 20, 2002, vol. 277, No. 51, pp. 49408-49416.
Chen, Y., et al., "HEC Binds to the Seventh Regulatory Subunit of the 26 S Proteosome and Modulates the Proteolysis of Mitotic Cyclins", The Journal of Biological Chemistry, Sep. 19, 1997, vol. 272, No. 38, pp. 24081, 24086-24087.
Chen, Y., et al., "HEC, A Novel Nuclear Protein Rich in Leucine Heptad Repeats Specifically Involved in Mitosis", Molecular and Cellular Biology, Oct. 1997, vol. 17, No. 10, pp. 6049-6056.

* cited by examiner

*Primary Examiner* — Karen Canella
(74) *Attorney, Agent, or Firm* — McKeon, Meunier, Carlin & Curfman, LLC

(57) ABSTRACT

The present invention provides methods and compounds for inhibiting HEC1 activity for the treatment of diseases involving cell hyperproliferation, e.g. cancer. The present invention also provides methods of identifying compounds for inhibiting HEC1 activity.

9 Claims, 21 Drawing Sheets

FIG.2A
| | colony color | β-Gal. activity |
|---|---|---|
| hsHec1 (a.a. 1-642) | | |
| 15Pst (a.a. 251-618) | blue | 2744 ± 220 |
| 15PR (a.a. 251-431) | blue | 902 ± 226 |
| 15Scs (a.a. 361-547) | blue | 637 ± 398 |
| 15HpBg (a.a. 547-618) | white | 17 ± 3 |
FIG.2B
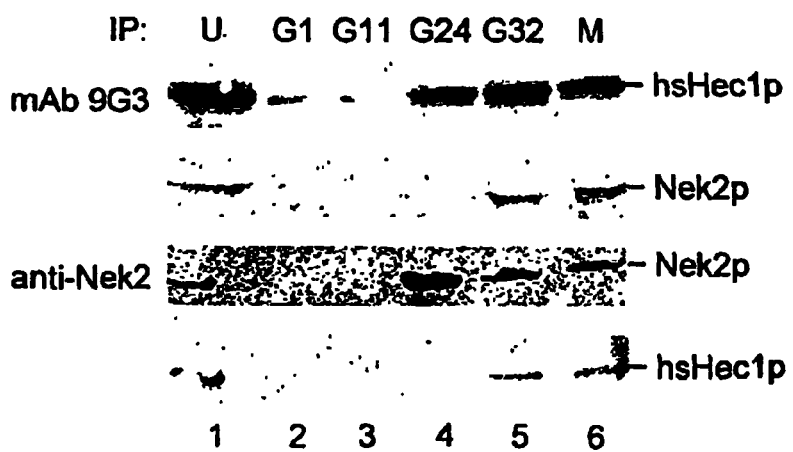
FIG.2C hsHEC1    158    LGYPFAL Ⓢ KSSMYTV
peptide sequence:    LGYPFAL$\underline{S^{PO4}}$KSSMYTV
(A439)
FIG.3A
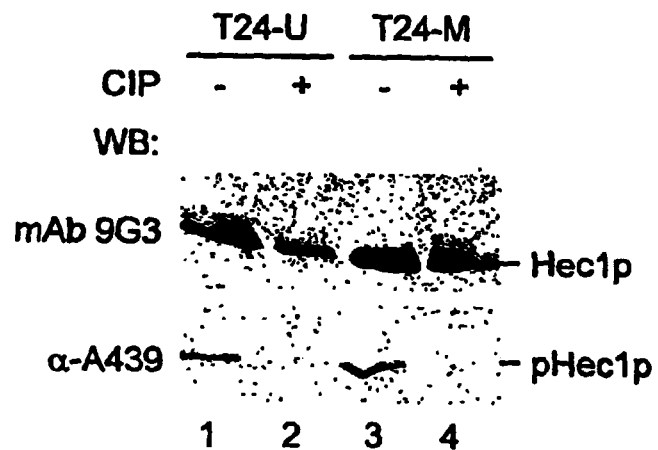
FIG.3B
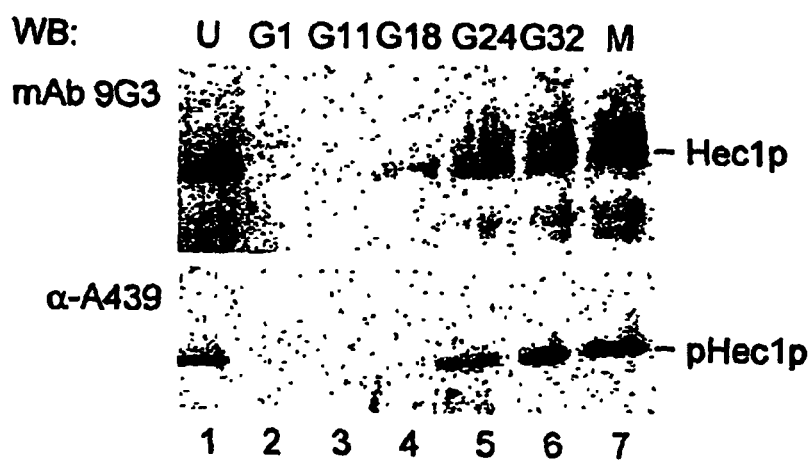
FIG.3C Nima     35 F I L C R K E I N Y I K Nek2     32 K I L V W K E L D Y G S scNeK2/Kin3    49 K I L C R K D I K Y G H

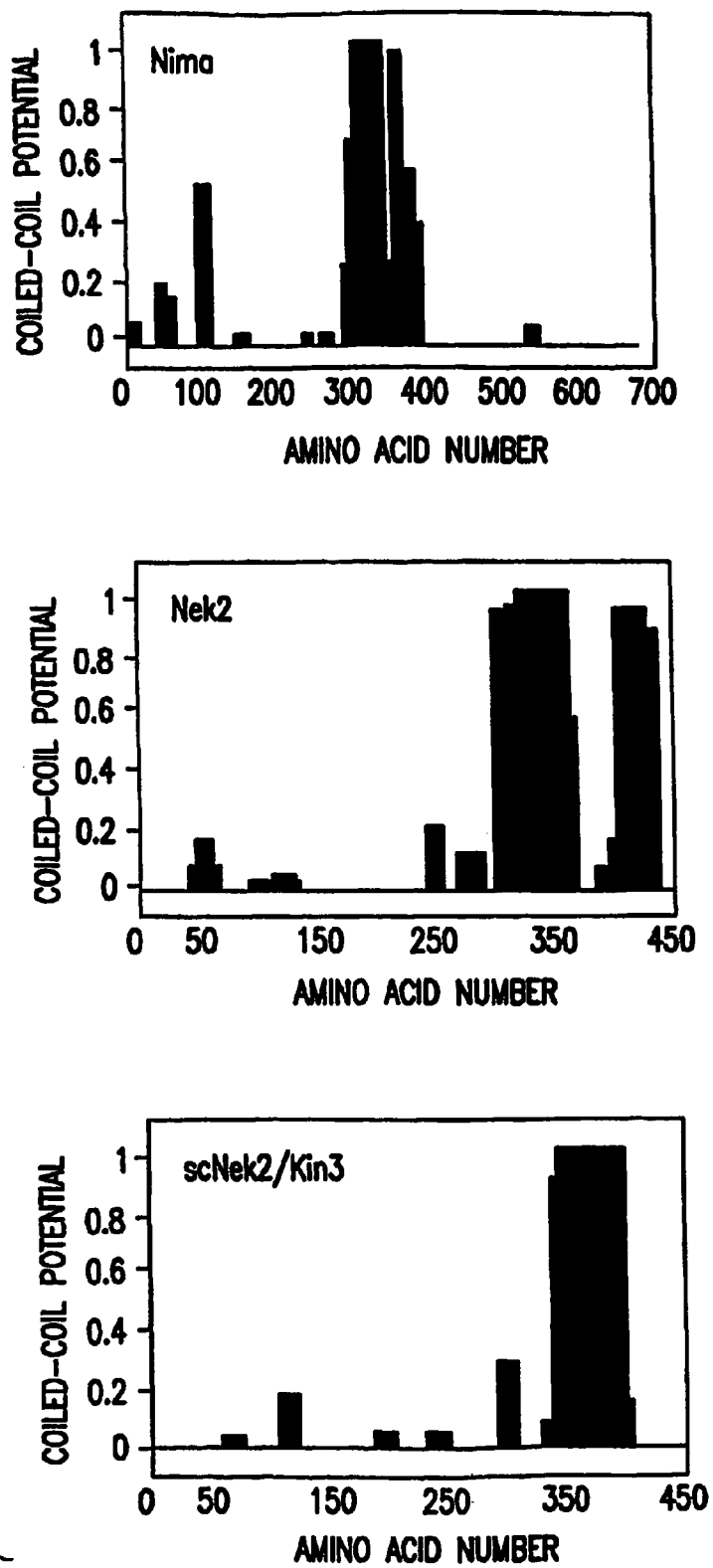

scHec1 192 KNLRYPFLESIN
scHec1S201A    KNLRYPFLEAIN
scHec1S201E    KNLRYPFLEEIN
hsHec1 156 KDLGYPEALSKS
hsHec1S165A    KDLGYPEALAKS
hsHec1S165E    KDLGYPEALEKS

IBT 4282
MW: 247.21

IBT 6432
MW: 249.27

IBT 11830
MW: 294.38

IBT 12008
MW: 399.08

IBT 13131
MW: 308.41

IBT 14664
MW: 382.49

IBT 15154
MW: 493.45

ND COMPOUNDS FOR
METHODS AND COMPOUNDS FOR INHIBITING HEC1 ACTIVITY FOR THE TREATMENT OF PROLIFERATIVE DISEASES

CROSS-REFERENCE TO RELATED APPLICATIONS

This application claims benefit of priority from U.S. Provisional Application No. 60/418,189, filed Oct. 11, 2002, which is herein incorporated by reference in its entirety.

STATEMENT OF GOVERNMENT SUPPORT

This invention was made with government support under grants CA058318 and CA081020 awarded by the National Institutes of Health (N1H). The government has certain rights in the invention.

FIELD OF INVENTION

The present invention generally relates to inhibition or modulation of Hec1 protein function to effect changes in the partitioning of chromosomes, to alter the viability of cells, and to alter the ability of dividing cells to yield viable daughter cells. More particularly, the disclosed invention relates to blocking particular interactions between Hec1 protein and Nek2 protein and/or Hec1 protein and Hint1 protein, small molecules that block the particular interactions, and methods of screening for small molecules or other therapeutic agents that block the interactions.

BACKGROUND OF THE INVENTION

Genetic instability, an important hallmark of cancer, can occur at two different levels. First, increased mutation rates can result from defective repair of damaged DNA or replication errors. Second, improper segregation of whole chromosomes or pieces of chromosomes during mitosis can lead to aneuploidy or translocations, traits commonly observed in cancer. Associations of oncoproteins or tumor suppressor proteins with the process of chromosome segregation provide links between chromosomal instability and carcinogenesis.

Hec1, a coiled-coil protein that is highly expressed in most cancer cells, appears to be crucial for faithful chromosome segregation. Cells microinjected with anti-Hec1 antibodies undergo aberrant mitosis, with grossly unequal distribution of chromosomes. Furthermore, Hec1 associates with several proteins required for G2/M phase progression, including components of the 26S proteasome, Smc1/2, and the NimA-like protein kinase Nek2. Nek2 has significant sequence homology with NimA, a serine/threonine kinase required for passage of fungi past G2 into M phase, exit from M phase, and response to DNA damage. A yeast homolog of HEC1 (scHec1) is essential for yeast survival and plays an important role in chromosome segregation. Human HEC1 (hsHec1) can fulfill all essential functions in S. cerevesiae null for scHec1, suggesting that fundamental mechanisms governing chromosome segregation are highly conserved in evolutionarily divergent species.

In view of the high incidence of cancers and the lack of efficacious treatments for many types of cancer, there is a need in the art for new therapeutic targets and new approaches for cancer treatment.

SUMMARY OF THE INVENTION

Hec1, a protein that is highly expressed in most cancer cells, plays an important role in chromosome segregation.

In accordance with the purposes of this invention, as embodied and broadly described herein, this invention, in one aspect, relates to a method of treating or preventing a disease of cell hyperproliferation, by blocking interaction between Hec1 protein and at least one further protein, thereby lessening cell hyperproliferation.

In a second aspect, the present invention relates to a method of treating or preventing a disease of cell hyperproliferation, by inhibiting phosphorylation of residue 165 of Hec1 protein, or a corresponding functional residue of a homolog of Hec1 protein, thereby lessening cell hyperproliferation.

In a third aspect, the present invention relates to a method of treating or preventing a disease of cell hyperproliferation, by reducing phosphorylation of amino acid residue 165 of Hec1 protein, or a corresponding functional residue of a homolog of Hec1 protein, thereby lessening cell hyperproliferation.

In a fourth aspect, the present invention relates to a method of treating or preventing a disease of cell hyperproliferation, by reducing phosphorylation of an amino acid residue other than residue 165 of Hec1 protein, wherein reduced phosphorylation prevents or lessens protein function characteristic of phosphorylated Hec1 protein.

In a fifth aspect, the present invention relates to a method of identifying a molecule that reduces an interaction between Hec1 protein and at least one further protein. The method can include: a) contacting Hec1 protein and the at least one further protein in the relative absence of a specified molecule; b) contacting Hec1 protein and the at least one further protein in the relative presence of a specified molecule; c) determining the relative amount of interaction between the Hec1 protein and the at least one further protein in a) and b); and d) comparing the relative amount of interaction, wherein if the relative presence of the specified molecule causes less interaction than the relative absence of the specified molecule, the specified molecule is determined to reduce interactions between the Hec1 protein and the at least one further protein.

In a sixth aspect, the present invention relates to a method of identifying a molecule that interferes with a function of Hec1 protein, Nek2 protein and/or Hint1 protein and reduce cell proliferation. The method can include: contacting a sample comprising proliferating cells with the molecule or a combination of molecules; and measuring the amount of cell proliferation, cell cycle progression, cell cycle arrest, or apoptosis in the sample exposed to the molecule or combination of molecules, whereby a decrease in cell proliferation, a decrease in cell cycle progression, an increase in cell cycle arrest, or an increase in apoptosis in the sample comprising proliferating cells exposed to the molecule or combination of molecules, relative to the amount of proliferation, cell cycle progression, cell cycle arrest, or apoptosis in a sample comprising proliferating cells not contacted with the molecule or combination of molecules, identifies a molecule or combination of molecules that inhibits proliferation of the cells.

In a seventh aspect, the present invention relates to a method for identifying a potential ligand of a Hec1 protein. The method can include: synthesizing the potential ligand; contacting the potential ligand with a Hec1 protein domain-containing protein; and determining whether the potential ligand binds to the Hec1 protein domain-containing protein.

In an eighth aspect, the present invention relates to a molecule or ligand identified by the methods of the fifth, sixth or seventh aspects of the invention, wherein the molecule or ligand identified lessens proliferation when contacted with proliferating cells.

In a ninth aspect, the present invention relates to a composition that includes a molecule or ligand of the eighth aspect of the invention and a pharmaceutically acceptable carrier, excipient, or diluent.

DESCRIPTION OF THE DRAWINGS

The accompanying drawings constitute a part of this specification and, together with the description, serve to explain the principles of the invention.

FIG. 1A. T24 cells were labeled with either $^{35}$S-methionine or $^{32}$P-orthophosphate and lysed. Lysates were immunoprecipitated with polyclonal anti-Hec1 antibodies (lanes 2 and 5), pre-immune sera (lanes 1 and 4), or monoclonal anti-Hec1 antibodies (mAb 9G3) (lane 6). The arrow indicates migration of the 76 kDa Hec1 protein.

FIG. 1B. Phospho-amino acid analysis of $^{32}$P-labeled Hec1. The radioactively labeled protein was isolated and subjected to amino acid hydrolysis. The lysates were analyzed by thin layer chromatography using phosphorylated serine, threonine, and tyrosine as standards. Hec1 is primarily phosphorylated on serine residues. Pi=unincorporated, labeled phosphate; Ori=original spot.

FIG. 1C. Cell cycle-dependent phosphorylation of Hec1. T24 cells released from density arrest at G1 (lane 3) were labeled with $^{32}$P-orthophosphate, lysed, and immunoprecipitated with mAb 9G3 at time periods corresponding to different phases of the cell cycle. Expression of Hec1 was detected by Western blotting with mAb 9G3, shown in the middle panel. (G11, 11 hours after release for G1; G18, 18 hours after release for G1/S; G24 for S phase; and G32 for G2/M phase). Phosphorylation of Hec1 (phsHec1p) is evident starting at S phase (lane 6, bottom panel) and becomes most prominent during M phase (lane 7, bottom panel). The phosphorylation pattern of $p110^{RB}$ was used to mark cell cycle progression (top panel) as previously described (Chen, P. L., et al. (1989) *Cell* 58, 1193-1198).

FIG. 2A-2C. Interaction between Nek2 and Hec1 by GST pull-down assay.

FIG. 2A. Sepharose beads bound with purified glutathione S-transferase (GST, lane 2) and GST fusions of Hec1 containing amino acids 56-642 (GST-hsHec1p, lane 3) or 251-618 (GST-15Pst, lane 4) were mixed with in vitro translated, $^{35}$S-methionine-labeled Nek2 (lane 1), then washed extensively. The binding complexes were separated by SDS-PAGE, dried, and visualized by autoradiography.

FIG. 2B. Specific regions of Hec1 bind to Nek2 by yeast two-hybrid assay. Deletion mutants containing the different coiled-coil domains of Hec1 were fused in-frame to a GAL4 DNA binding domain. Nek2 was expressed as a GAL4 transactivation domain fusion. Yeast transformants with these two hybrid proteins were grown in liquid cultures and used for O-nitrophenyl-β-galactopyranosidase quantitation of β-galactosidase activity. The fold-increase in activity compared to the host yeast strain Y153 is indicated. Assays were done in triplicate for each transformation.

FIG. 2C. Cell cycle-dependent interaction between Hec1 and Nek2. T24 bladder carcinoma cells were first density arrested at G1 (lanes 2) and then released for re-entry into the cell cycle. At different time points after release from density arrest (indicated above the lanes), cells were collected and lysed. The clarified lysates were immunoprecipitated with mAb9G3 anti-Hec1 monoclonal antibodies (upper two panels) or anti-Nek2 antisera (lower two panels). Hec1 and Nek2 co-immunoprecipitated at G2 and M phases (lanes 5 and 6).

FIG. 3A-3C. Hec1 is phosphorylated on serine 165 in vivo.

FIG. 3A. Potential Nek2 recognition sequence including serine 165 of Hec1 and the chemically synthesized phosphopeptide (A439) used as antigen for generating specific antibodies.

FIG. 3B. Anti-A439 antibodies recognize the phosphorylated Hec1. T24 cells, either unsynchronized (lanes 1 and 2) or treated with nocadozole to arrest them at G2/M (lanes 3 and 4), were lysed and immunoprecipitated with mAb9G3. The immunoprecipitates were either not treated (lanes 1 and 3) or treated with calf intestine phosphatase (CIP) (lanes 2 and 4), separated by SDS-PAGE, and subjected to Western blotting probed with mAb 9G3 (upper panel) or anti-A439 antibodies (lower panel). Anti-A439 antibodies recognized the untreated but not CIP-treated Hec1.

FIG. 3C. Expression of the phosphorylated Hec1 detected by anti-A439 antibodies during cell cycle progression. T24 cells in different synchronized stages of the cell cycle were prepared as described above. Hec1 was detected by straight Western blotting with either mnAb 9G3, (upper panel; G11, 11 hours after release for G1, G18; 18 hours after release for G1/S; G24 for S phase; G32 for G2/M phase), or by anti-A439 antibodies (lower panel).

FIG. 4A. Purification of His-tagged Hec1. 6×His tagged full-length Hec1 was expressed in *E. coli* using the PET expression system. The total bacterial lysate (lane 1) was passed through a DEAE Sepharose column and the flow-through (lane 2) was then bound to an SP Sepharose column. Hec1 eluted with NaCl gradient fractions between 200 and 300 mM. The eluant was then loaded onto Ni-sepharose column and eluted with 60 mM imidozole (lane 4). This eluant was loaded onto an Sephadex 300 column (lane 5) to obtain nearly pure Hec1. Hec1 from different steps of the purification was subjected to SDS-PAGE, then stained with Coomassie blue. Hec1S165A was purified by an identical scheme; the final purified product is shown in lane 6.

FIG. 4B. Expression of His-tagged Nek2 in a baculovirus system. Baculovirus carrying the 6×His full-length Nek2 was generated as described in Experimental Procedures. Cell lysates from infected (lanes 2 and 3) or uninfected (lane 1) sf9 cells were probed with anti-Nek2 antibodies to demonstrate the specificity of the anti-Nek2 antibodies. The antibodies specifically recognize the recombinant Nek2 protein but not proteins from uninfected sf9 cells.

FIG. 4C. Nek2 phosphorylates Hec1. Kinase reactions were performed with $^{32}$P-γ-ATP to assess the activity of immunopurified Nek2 kinase, using either wild-type Hec1 (lane 3) or Hec1S165A mutant (lane 5) as the substrate. Additional control reactions carried out either by using pre-immune antisera to purify the Nek2 (lane 1), heat-inactivated Nek2 (lane 4), or without substrate (lane 2) failed to detect radioactively labeled Hec1 protein.

FIG. 4D. Anti-A439 antibodies recognize Hec1 phosphorylated in vitro by Nek2. Purified Hec1 or Hec1 S165A was either left unphosphorylated (lanes 1 and 3) or phosphorylated with Nek2 (lanes 2 and 4), using cold ATP, and analyzed by Western blotting with either mAb 9G3 antibody (upper panel) or anti-A439 (lower panel). Phosphorylated Hec1 was detected by anti-A439.

FIG. 5A-5D. Yeast Kin3 shares properties with Nek2.

FIG. 5A. Primary sequence homology comparison between NimA, Nek2, and Kin3.

FIG. 5B. Comparison of the coiled-coil regions in NimA, Nek2, and Kin3, using a program found at www.isrec.isb-sib.ch/software/software.html.

FIG. 5C. Nek2 or Kin3 binds to hsHec1 and scHec1 by GST pull-down assay. GST (lanes 2 and 7), GST fusions of a small N-terminal hsHec1 (a.a. 56-128, GST-15Bgl, lanes 3 and 8), a longer portion of hsHec1 (a.a. 56-618, GST-Hec1, lanes 4 and 9), and a long N-terminal portion of scHec1 (a.a. 1-691, GST-scHec1) (lanes 4 and 8) were prepared and used to bind to in vitro translated Nek2 (lane 1) or Kin3 (lane 6). Nek2 and Kin3 (scNek2) both bind to hsHec1 and scHec1.

FIG. 5D. Partial sequence of NimA showing the glutamic acid residue at amino acid position 41. Comparison of homologous sequences in Nek2 and Kin3, with glutamic acid at amino acid residue 38 (Nek2) and aspartic acid at amino acid residue 55 (Kin3).

FIG. 6A. Temperature sensitive growth of yeast carrying kin3D55G. YPH499 is the wild-type yeast strain. WHL6001 is a yeast strain with a null allele for kin3. WHL6009 was derived from WHL6001; it contains kin3D55G under control of the Kin3 promoter in a CEN.ARS construct. WHL101 contains hsHec1 to replace scHec1. WHL6012 was derived from WHL101; it contains kin3D55G under control of the Kin3 promoter in a CEN/ARS construct. These yeast strains were spotted on triplicate plates and grown at two different temperatures. One of the plates originally at 37° C. was shifted to room temperature (25° C.). Both WHL6009 and WHL6012 were reversibly temperature sensitive. The growth of these mutant strains was temperature dependent regardless of the Hec1 status. WHL6001 grew like wild type YPH499.

FIG. 6B. Expression of the nek2E38G mutant in WHL6001 leads to temperature sensitive growth. Nek2E38G was introduced into kin3 null cells (WHL6001) under control of the Kin3 promoter in a CEN.ARS construct to create strain WHL6001. The growth of this yeast strain was temperature sensitive.

FIG. 6C. Overexpression of the wild type Kin3 (strain WHL6014) or Nek2 (strain WHL6015) partially suppressed temperature sensitivity of WHL6009, which carries the Kin3D55G mutant.

FIG. 7A-7B. Production and specificity of anti-Kin3p antibodies. Full-length Kin3 cDNA was fused to GST in-frame and the resulting GST-Kin3 fusion protein was used to immunize mice. After several boosts, anti-Kin3 anti-sera were collected and used to immunoprecipitate in vitro translated full-length kin3 protein. Pre-immune serum failed to immunoprecipitate in vitro translated Kin3p (FIG. 7A, lane 2), while immune serum was able to immunoprecipitate it (FIG. 7A, lane 3). Detection of Kin3p from wild-type yeast cells using anti-Kin3p sera identified Kin3p as a 46 kDa protein (FIG. 7B, lane 1) and the anti-Kin3p anti-sera was specific for kin3p since it failed to detect Kin3 in lysate prepared from kin3 null cells (FIG. 7B, lane 2).

FIG. 7C. scHec1p and Kin3 interact at nonpermissive temperature. YPH499 (wild-type) or WHL6009 (kin3D55G mutant) strains were grown at 25° C. for 4 hours before shifting to 37° C. for 8 more hours. The cells were harvested and lysed for immunoprecipitation with anti-scHec1 antibodies (lanes 1 to 4) and Western blotted with anti-scHec1 anti-sera (upper panel) or anti-Kin3 antisera (lower panel). scHec1 interacts with Kin3 at permissive and nonpermissive temperature in both wild-type and kin3D55G cells.

FIG. 7D. Interaction between hsHec1 and Kin3 at nonpermissive temperature in WHL6012 cells. WHL101 (schec1 null rescued by hsHec1) or WHL6012 (same mutant with additional kin3D55G mutation) cells were cultured as described for FIG. 7C. The clarified lysates were immunoprecipitated with anti-hsHec1 mAb 9G3 antibodies (lanes 1 to 4) and Western blotted with mAb 9G3 antibodies (upper panel) or anti-Kin3 antisera (lower panel). hsHec1 interacted with Kin3 at permissive and nonpermissive temperature in both yeast strains.

FIG. 7E. Phosphorylation of Hec1 is abolished at nonpermissive temperature in WHL6012 cells. WHL101 (lane 1 and 2) or WHL6012 (lane 3 and 4) cells were prepared as described in C. The cells were harvested and lysed in the presence of phosphatase inhibitors. The clarified lysates were immunoprecipitated with mAb 9G3 and Western blotted with mAb 9G3 (upper panel) or monoclonal anti-A439 antibodies, mAb 4F9 (lower panel). hsHec1 was not phosphorylated in WHL6012 cells at nonpermissive temperature.

FIG. 8A. Hec1 phosphorylation site for Nek2. The potential NEK2 phosphorylation site at HEC1 (S165) was mutated into Ala (S165A) or Glu (S165E).

FIG. 8B. hsHec1S165A fails to rescue the survival of cells null for scHec1. Only the hsHec1S165E mutant, which mimics the negative charge created by serine phosphorylation, and wild-type Hec1 were able to rescue yeast deficient for schec1.

FIG. 8C. Plating efficiency of yeast rescued by wild-type hsHec1 (WHL101) or by hsHec1S165E (WHL-SE). Two hundred cells from log-phase cultures were plated onto solid plates. The surviving cells were scored for colonies formed on plates after 3 days in culture at 30° C. The results are shown as means±S.E.M. from three independent experiments.

FIG. 9A. Diagram of the structure of Hint1. There are two distinct coiled-coil domains in the middle of the protein.

FIG. 9B. Result from GST-pull down assay. Sepharose beads bound with purified glutathione S-transferase (GST, lane 2) and GST fusions of Hint1 (GSTHint1, lane 3), aa80-155 (GST-Hint1-A, lane 4), or aa 170-220 (GST-Hint1-B, lane 5) were mixed with the in vitro translated, 35S-methionine-labeled HEC1 (lane 1), followed extensive washing. The binding complexes were separated by SDS-PAGE, dried, and visualized by autoradiography.

FIG. 13A. Dissociation of Hec1 and Nek2 in INH1I-treated cells. HeLa cells were grown in log-phase and treated with 0.08% DMSO or with the indicated concentration of INH1 for 24 hours. Cells were harvested for immunoprecipitation with the anti-Hec1 antibody mAb 9G3. The immunoprecipitates were analyzed by western blot with either mAb 9G3 or anti-Nek2 antibodies. In cells treated with 10 or 20 µM of INH 1, Nek2 failed to be co-immunoprecipitated with Hec1 (lanes 4 and 5). Fractions of lysates were taken for straight western blot with anti-Rad50 antibodies as a loading control.

FIG. 13B. Nek2 phosphorylation of Hec1 was inhibited in INH1/2 treated cells.

Figure 1A:
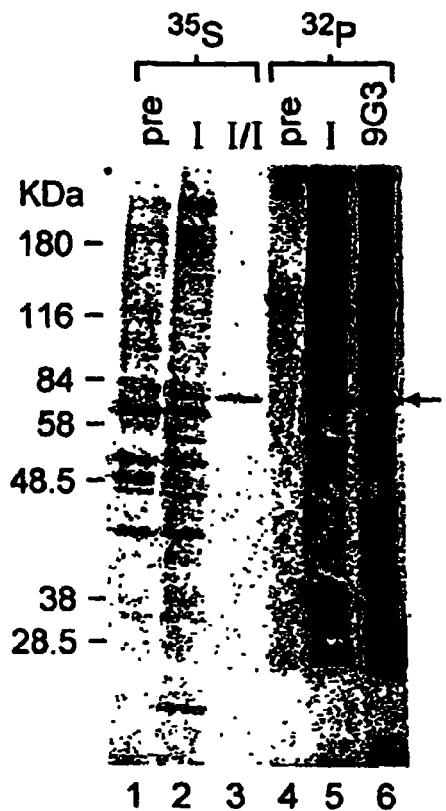
FIG. 1A-1C. Cell cycle dependent serine phosphorylation of Hec1.

HeLa cells (lane 1) were treated with 0.08% DMSO (lane 2), 20 µM of INH1 (lane 3), INH2 (lane 4) or nocodazole (lane 5) for 36 hours before cells were harvested for immunoblotting with anti-Hec1, mAb9G3, for total Hec1 protein or anti-A439 for the phosphorylated Hec1 at S165 (pHEC1). Nek2 phosphorylation of Hec1 is undetectable in INH1 and INH2 treated cells (lanes 3 and 4).

Figure 14A:
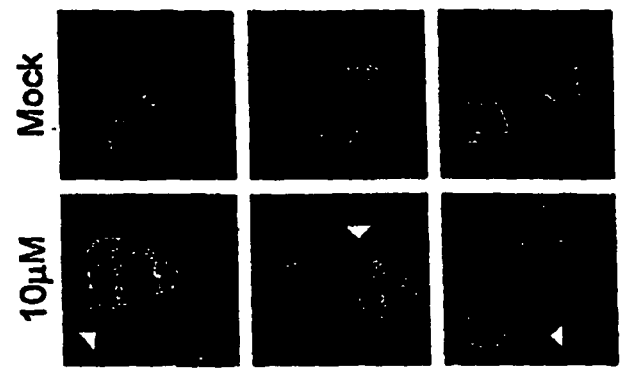
Figure 14B:
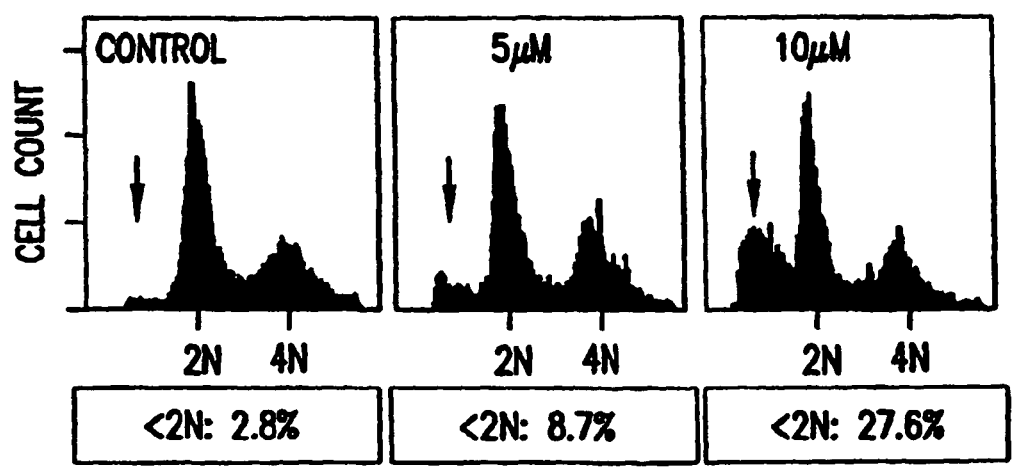

FIG. 14A-14B. Phenotypes of HeLa cells treated with INH1.

FIG. 14A. Micrographic pictures of H2B-GFP labeled HeLa cells treated with DMSO (Mock) or 10 mM of INH1. White arrows indicate lagging chromosomes during M phase.

FIG. 14B. Flow cytometric analysis of INH1 treated HeLa cells. Exponentially grown HeLa cells were seeded at 5×10$^5$ cells per 10-cm dish for 24 hrs and then treated with DMSO (control) or 5 or 10 µM of INH1 for 72 hrs. Cells were harvested and fixed in 70% ethanol for flow cytometry after staining with propidium iodide. Data represent one of three independent experiments.

Figure 15:
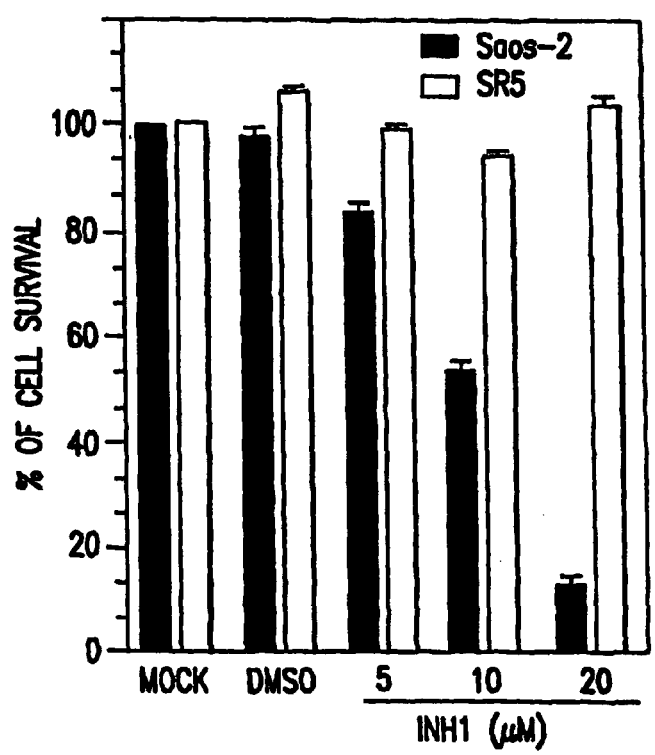

FIG. 15. Differential effect of INH1 in Rb positive and negative osteosarcoma Saos2 cells. Cells grown in log-phase were either untreated or treated with 0.08% DMSO or INH1 at the indicated concentrations for 60 hours. Surviving cells were counted by trypan blue exclusion and expressed as a percentage of the control. SR5 is a Rb reconstituted Saos-2 cell line. The values were the average of a triplicate set of experiments, with error bars representing the SEM.

Figure 16:
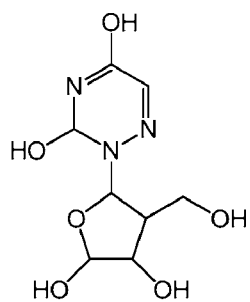
Figure 16:
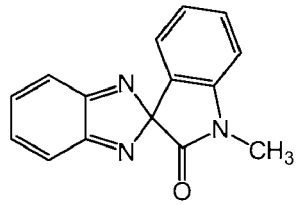
Figure 16:
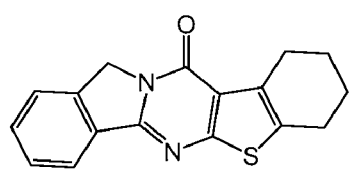
Figure 16:
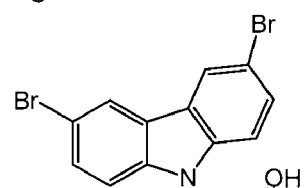
Figure 16:
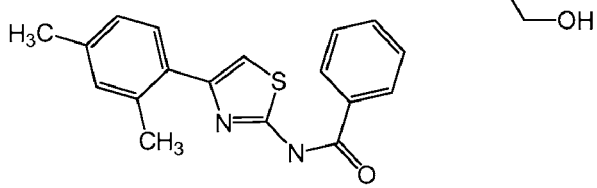
Figure 16:
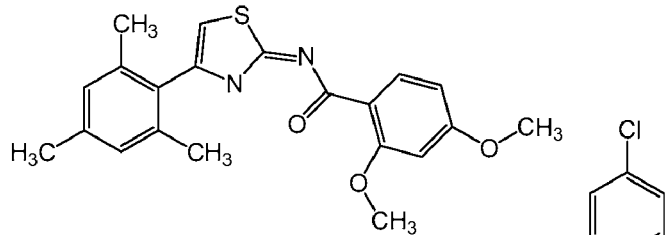
Figure 16:
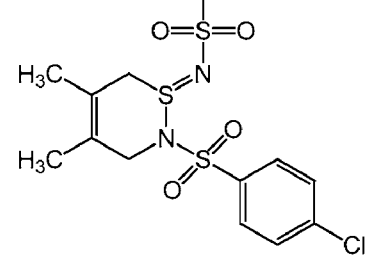

FIG. 16. Exemplary compounds that can be used to inhibit phosphorylation of Hec1 serine 165. Such compounds include IBT4282, IBT6432, IBT11830, IBT12008, IBT13131, IBT14664 and IBT15154, shown herein.

Figure 17:
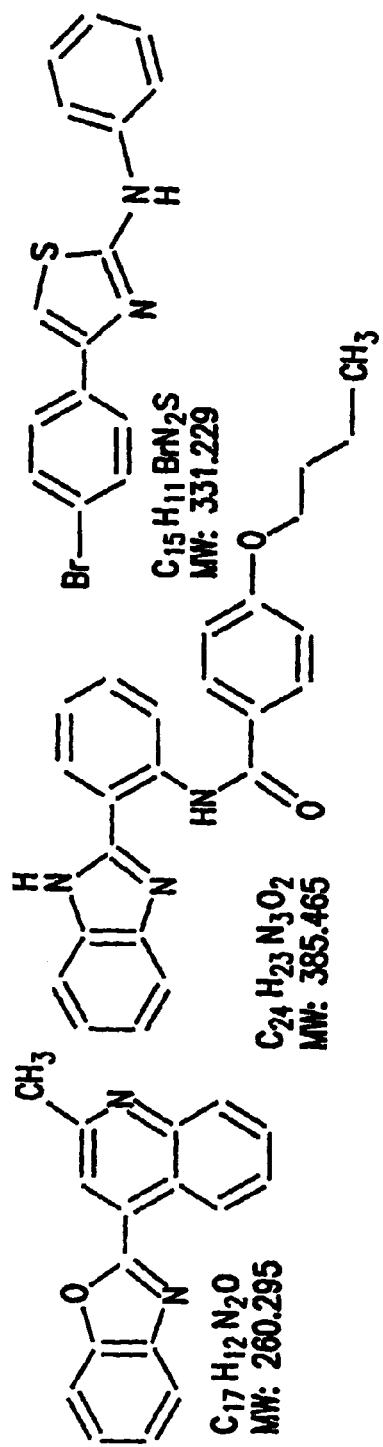

FIG. 17. Structures and molecular weights of three compounds the Interfere with the Interaction between Hec1 and Nek2, as detected by reverse two-hybrid assay.

DESCRIPTION OF THE INVENTION

Hec1 (highly expressed in cancer) plays essential roles in chromosome segregation by interacting through its coiled-coil domains with several proteins that modulate the G2/M phase of the cell cycle. Hec1 localizes to kinetochores and its inactivation, either by genetic deletion or antibody neutralization, leads to severe and lethal chromosomal segregation errors, indicating that Hec1 plays a critical role in chromosome segregation. The mechanisms by which Hec1 is regulated, however, are not known.

The present invention is based upon our discovery, as described herein, that human Hec1 is a serine phosphoprotein that binds specifically to the mitotic regulatory kinase Nek2 during G2/M. Nek2 phosphorylates Hec1 on serine residue 165, both in vitro and in vivo. Yeast cells are viable without Kin3p, a close structural homolog of Nek2 that binds to both human and yeast Hec1. However, when yeast carry a Kin3 (D55G) or Nek2 (E38G) mutation to mimic a similar temperature-sensitive nima mutation in *Aspergillus*, their growth is arrested at the non-permissive temperature because the Kin3 (D55G) mutant binds to Hec1 but fails to phosphorylate it. Whereas wild-type human Hec1 rescues lethality resulting from deletion of yeast Hec1 in *S. cerevisiae*, a human Hec1 mutant changing Ser 165 to Ala does not. A mutation changing Ser 165 to Glu to mimic the negative charge created by phosphorylation partially rescues lethality but results in a high incidence of errors in chromosomal segregation. These results suggest that cell cycle-regulated phosphorylation of Hec1 on Ser 165 by Nek2 is essential for faithful chromosome segregation.

The search for good molecular targets for cancer therapy is an ongoing struggle in cancer research. In this regard, Hec1 has several suitable characteristics of a good therapeutic target. First, Hec1 is overexpressed in many cancer cell lines, including those from retinoblastoma, cervical carcinoma, breast cancer, and colon cancer, as compared to rapidly growing non-cancerous cell lines. Second, Hec1 is specifically expressed at late S phase to M phase of the cell cycle. Third, Hec1 has a critical function in chromosome segregation and inactivation of Hec1 leads to cell death. Hec1 thus offers a unique target for molecular intervention. We have meticulously characterized partners of Hec1 and demonstrated that the phosphorylation of Hec 1 by Nek2 is critical for its function. With this characterization, we have determined that small molecules that inactivate Hec1 function, by interrupting the critical interaction between Hec1 and Nek2, can be used as (or to develop) therapeutic compounds to treat diseases and conditions of cellular hyperproliferation, e.g., cancer. Because these small molecules are targeted to Hec1/Nek2, which play a critical role in chromosome segregation, the use of these types of small molecules will function via a different molecular pathway from current drugs, such as taxol, which disturbs chromosome segregation by stabilizing microtubules. The present invention allows the creation and testing of a novel class of molecules that can be used by themselves, or that can be used to complement those existing drugs that act by a different molecular mechanism.

It is to be understood that this invention is not limited to specific methods, specific compounds, specific solutions, or to particular devices, as such may, of course, vary. It is also to be understood that the terminology used herein is for the purpose of describing particular embodiments only and is not intended to be limiting. Throughout the specification and claims, reference will be made to a number of terms which shall be defined to have the following meanings:

As used in the specification and the appended claims, the singular forms "a," "an" and "the" include plural referents unless the context clearly dictates otherwise. Thus, for example, reference to "polypeptide" includes mixtures of polypeptides, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

"Amino acid," as used herein, means the typically encountered twenty amino acids which make up polypeptides. In addition, it further includes less typical constituents which are both naturally occurring, such as, but not limited to formylmethionine and selenocysteine, analogs of typically found amino acids, and mimetics of amino acids or amino acid functionalities.

"Cell hyperproliferation," as used herein, means cell proliferation that is greater than normal. For example, cancer is a disease of cell hyperproliferation.

"Analogous," as used herein, particularly to describe a structure, means that the structure has characteristic properties like that of another structure, even though there may be substantial differences between the structures as a whole or between significant portions of the structures.

"Analog," as used herein, has the commonly accepted meaning within the art. In particular, it refers to those compounds which have certain similarities in structure, function, and/or properties to the species of which they are an analog. By way of illustration, the commonly known nucleoside analogs such as AZT, ddI, ddC, and d4T have both structural and functional similarity to normal nucleosides. Similar relationships between polypeptides or small molecule compounds and their corresponding analogs are also recognized by those of skill in the art.

"Mimetic," as used herein, includes any molecules, e.g., any synthetic or naturally occurring molecule, the functional activity of which mimics that of a molecule useful in the methods of the invention. For example, one can model predicted chemical structures to mimic the structure of a binding region, such as a binding loop of a peptide. Such modeling can be performed using standard methods (see for example, Zhao et al., *Nat. Struct. Biol.* 2: 1131-1137 (1995)). Mimetics identified by method such as this can be further characterized as having the same binding functions as the originally identified molecule of interest according the binding assays or modeling methods described herein. Mimetics can also be identified by screening libraries of synthetic or naturally occurring compounds, e.g., but not limited to, combinatorial chemical libraries (see, e.g., Ostresh et al., *Proc. Natl. Acad. Sci. U.S.A.* 91: 11138-11142 (1994); Domer et al., *Bioorg. Med. Chem.* 4: 709-715 (1996); Eichler et al., *Med. Res. Rev.* 15: 481-496 (1995); Blondelle et al., *Biochem. J.* 313: 141-147 (1996); Perez-Paya et al., *J. Biol. Chem.* 271: 4120-4126 (1996)). Mimetics can also be designed by modifying or derivatizing the chemical structure of a compound identified as having a desirable functional activity (e.g., inhibition of phosphorylation of Hec1 serine 165) useful in the methods of the present invention, as will appreciated by those of skill in the art. Examples of such identified compounds include IBT4282, IBT6432, IBT11830, IBT12008, IBT13131, IBT14664 and IBT15154 (FIG. 16).

"Bind," as used herein, means the well-understood interaction between two species of molecules, e.g., the interaction between a polypeptide and a ligand or the interaction between a protein and a dye molecule. "Specifically bind," as used herein, describes interactions between two molecular species wherein a member of the binding pair does not substantially cross-react with other molecules not identical, or substantially similar to, or analogous to the other member of the binding pair. Specific binding is often associated with a particular set of interactions which form between the members of the binding pair.

"Protein domain," as used herein, has the well-known meaning of the art used to classify and characterize protein structure. As the term is normally used, protein domains are considered to be compact, local, semi-independent units of protein structure. In a multi-domain protein, the domains can make up functionally and structurally distinct modules. These modules are usually formed from a single continuous segment of a polypeptide chain or region of amino acid sequence.

"Deletion," as used herein, refers to a change in an amino acid or nucleotide sequence in which one or more amino acid or nucleotide residues, respectively, are absent relative to the reference sequence.

"Insertion" or "addition," as used herein, refers to a change in an amino acid or nucleotide sequence resulting in the addition of one or more amino acid or nucleotide residues, respectively, as compared to the reference sequence.

"Substitution," as used herein, refers to the replacement of one or more amino acids or nucleotides by one or more different amino acids or nucleotides, respectively, in a reference sequence.

"Isolated," as used herein refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state.

"Purified," as used herein, refers to species, such as polypeptides, that are removed from their natural environment, isolated or separated, and are at least 60% free from other components with which they are normally associated or components similar to those with which they are normally associated. It is preferable that they be more free from other components than to be less free from other components. For example, more preferably they are more than 70%, 75%, 80%, 85%, 90%, 95%, 97%, 98%, or 99% free from other components.

"Substantially similar," as used herein, refers in one aspect to polypeptides or portions thereof which have structures that are closely related to a reference polypeptide. When it is used in this context, "substantially similar" includes accommodation of specific differences mandated by specific differences between the molecular species compared. For example, two polypeptide structures having the same structural motif, but with different amino acid sequence, are substantially similar. Likewise, two polypeptide structures having the same overall motif, but wherein there are regions of variance between the two structures can also be classified as substantially similar depending upon the degree of variance and the fraction of the structure over which it occurs. As will be recognized by those of skill in the art, substantially similar can also be used to refer to properties of different species, such as, different drug molecules.

Conservative amino acid substitutions are well-known in the art, and include substitutions made on the basis of similarity in polarity, charge, solubility, hydrophobicity, hydrophilicity, amphipathicity and other factors. It is further recognized by those of skill in the art that substitutions, additions or deletions of a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It will further be recognized that certain substitutions, additions, and/or deletions can result from adoption of nucleic acid sequences that are advantageous for providing convenient cloning, restriction endonuclease and/or other features used by those of skill in the art. Further, there exist substitutions, addition and/or deletions which can be used to provide features useful in the purification of the polypeptide, such as is described herein with respect to a histidine tag but which applies equally well to other features.

Substitutions, additions, and/or deletions to the domains of Nek2, Hint1, or Hec1 proteins, and/or the sequence disclosed herein, which result in structures that are analogous to those of Nek2, Hint1, or Hec1 protein structure or properties described herein or portions thereof are specifically contemplated. Further, substitutions, additions and/or deletions to the proteins or portions thereof which result in structures which are substantially the same as the structure disclosed herein or portions thereof are also specifically contemplated. Any such modified structure is contemplated to be an example of a Nek2 protein, if derived from or having properties like those of a Nek2 protein, an example of a Hint1 protein, if derived from or having properties like those of a Hint1 protein, or an example of a Hec1 protein, if derived from or having properties like those of a Hec1 protein.

It should be noted that structures, constructs, or engineered proteins comprising portions of the Hec1, Nek2, or Hint1 proteins, or variants thereof, need not retain the activity of the proteins or domains from which they are derived. It is specifically contemplated that certain mutants and variants of the disclosed structures will retain structures and/or activities substantially similar to and or analogous to those of the disclosed structures, but will not have other features or activities that are typically associated with the non mutant or the non-varied species. Such other features or activities can include the ability to bind or interact with other molecules or to compete with other molecules for binding. As will be recognized by those of skill in the art, an engineered construct comprising a portion of Hec1 protein can be used to screen for a small molecule or other molecule that will interact with Hec1 protein or which will prevent interaction of Hec1 with another protein such as, but not limited to Nek2 and Hint1 proteins. For example, immobilized Hec1 protein or analog thereof can be contacted with a molecule of interest such as a small molecule drug. Binding of the molecule of interest can be determined directly by methods known to those of skill in the art.

Alternatively, immobilized Hec1 protein or analog thereof can be contacted with a molecule of interest and another protein that acts as a binding partner of Hec1. For example, the other protein that acts as a binding partner of Hec1 protein can be Nek2 protein or Hint1 protein. Alternatively, if the binding or interaction of an other protein causes the modification of Hec1 protein, such as phosphorylation of Hec1 protein, disruption of the interaction between Hec1 protein and the other protein can be monitored by determination of the level of phosphorylation of Hec1 protein after a period of time. As will be recognized by those of skill in the art, many other methods of determining the relative presence or relative absence of interactions between Hec1 protein and other proteins or the ability of agents to effect the relative presence or relative absence of interactions between Hec1 protein and other proteins are well within the abilities of those of skill in the art.

"Portion," as used herein, refers to the common meaning of the term as used by those of skill in the art. Specifically, a portion of an amino acid sequence includes any amino acid sequence which comprises the portion and any further sequence.

"Ligands" as defined herein can include antibodies generated against peptides of the present invention or reactive against the polypeptides of the present invention. Use of these antibodies for the purposes of characterizing the polypeptides of the invention is contemplated. Use of these antibodies, which can bind to proteins or polypeptides to form antibody-containing complexes, is also contemplated. Ligands that bind to Hec1 protein, Nek2 protein, or Hint1 protein can block interaction or reduce interaction of the protein with other proteins or molecules. Ligands that bind to Hec1 protein, Nek2 protein, or Hint1 protein can prevent other proteins or molecules from modifying the Hec1 protein, Nek2 protein, or Hint1 protein by blocking interaction or reducing interaction of the specified protein with other proteins that modify the specified protein. For example, modification of the specified protein by phosphorylation can be reduced. Alternatively, if the specified protein is phosphorylated, the dephosphorylation of the protein can be reduced.

The antibodies of the present invention which specifically bind the polypeptides of the present invention or portions thereof can include polyclonal and monoclonal antibodies which can be, e.g., intact immunoglobulin molecules, chimeric immunoglobulin molecules, or Fab or F(ab')$_2$ fragments. Such antibodies and antibody fragments can be produced by techniques well known in the art which include those described in Harlow and Lane ("Antibodies: A Laboratory Manual" Cold Spring Harbor Laboratory, Cold Spring Harbor, N.Y., (1989)) and Kohler et al. (*Nature* 256: 495-97 (1975); and U.S. Pat. Nos. 5,545,806, 5,569,825 and 5,625,126, herein incorporated by reference. The antibodies can be of any isotype IgG, IgA, IgD, IgE and IgM.

The present invention can also include single chain antibodies (ScFv), comprising linked VH and VL domains and which retain the conformation and specific binding activity of the native idiotype of the antibody. Such single chain antibodies are well known in the art and can be produced by standard methods (see, e.g., Alvarez et al., *Hum. Gene Ther.* 8: 229-242 (1997)).

Conditions whereby an antigen/antibody complex can form as well as assays for the detection of the formation of an antigen/antibody complex and quantitation of the detected protein are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., eds., Current Protocols in Immunology, Wiley, New York (1995)), agglutination assays, flocculation assays, cell panning, etc., as are well known to those of skill in the art. Examples of such assays that can determine the relative presence or absence of interactions between Hec1 protein and other proteins include those wherein either Hec1 protein or a protein that interacts with Hec1 protein is specifically bound by an antibody specific for the protein to which the antibody binds. In certain aspects, more than one such specific antibody can be used. In particular aspects, one or more antibodies specific for Hec1 protein and a second or further antibody specific for a binding partner of Hec1 protein can be used to determine the presence of both Hec1 protein and the binding partner of Hec1 protein in a complex one with another.

The antibody of this invention can be bound to a substrate (e.g., beads, tubes, slides, plates, nitrocellulose sheets, etc.) or conjugated with a detectable moiety or both bound and conjugated. The detectable moieties contemplated for the present invention can include, but are not limited to, a fluorescent moiety (e.g., fluorescein, rhodamine), a radioactive moiety (e.g., $^{32}P$, $^{125}I$, $^{35}S$), an enzyme moiety (e.g., horseradish peroxidase, alkaline phosphatase), a colloidal gold moiety and a biotin moiety. Such conjugation techniques are standard in the art (see, e.g., Harlow and Lane, "Antibodies, A Laboratory Manual" Cold Spring Harbor Publications, New York, (1988); Yang et al., Nature 382: 319-324 (1996)). The antibodies for domains of the Hec1, Hint1 or Nek2 proteins or fragments, analogs or mimetics thereof can be used to bind to polypeptides in vitro or in vivo. When the antibody is coupled to a label which is detectable but which does not interfere with binding to the protein domain or fragments thereof, the antibody can be used to identify the presence or absence of accessible domains. Labels can be coupled either directly or indirectly to the disclosed antibodies. One example of indirect coupling is by use of a spacer moiety. These spacer moieties, in turn, can be either insoluble or soluble (Diener et al., Science 231: 148 (1986)). Use of multiple antibodies, each specific for different proteins, can be used to identify interactions between different particular proteins as will be recognized by those of skill in the art.

Other ligands, such as small molecule ligands, can be identified by detection of binding directly to the target protein or the targeted domain of a protein. Methods to identify such binding events are well known to those of skill in the art. Alternatively, ligand binding can be detected by observation of reduced binding of a binding partner that would normally bind in the absence of the bound small molecule ligand. Alternatively, small molecule ligand binding can be detected by observation of effects on the state of the protein to which the ligand binds that are not observed when the ligand does not bind to the protein. For example, if binding of a ligand alters the level of phosphorylation of the protein, observation of an altered state of phosphorylation can be used to determine that the ligand bound to the protein.

There are many different labels and methods of labeling known. As will be recognized by those of skill in the art, many different types of labels can be used in the practice of the present invention. In its broadest sense, "label," as used herein, means a label or moiety that is detectable, i.e., that allows its presence or absence to be determined. Examples include any such label or moiety which will allow visual detection of the label, either in solution, as a localized population, or as a resulting precipitate. A label further includes any substance or moiety which will allow detection of a color change, visual detection by microscopy, or automated detection by spectrometry, radiometric measurement or the like. Examples of detectable labels include, but are not limited to, colorimetric labels, chemically reactive labels, fluorescence labels, enzymic labels and radioactive labels. Colorimetric particles of the invention may be gold particles, silver particles, platinum particles, copper particles, latex particles, hydrophobic dyes, and encapsulated dyes. It is preferred that the colorimetric particle is a gold sol particle.

Those of ordinary skill in the art will know of other suitable labels for binding to the protein, antibody, or ligand of interest, or will be able to ascertain such, using routine experimentation. Furthermore, the binding of these labels to the molecule of the invention or the molecule used in practice of the invention can be done using standard techniques common to those of ordinary skill in the art.

For in vivo detection, radioisotopes may be bound either directly or indirectly to the species to be labeled by using an intermediate functional group. Intermediate functional groups which often are used to bind radioisotopes which exist as metallic ions to functional molecules are the bifunctional chelating agents such as diethylenetriaminepentacetic acid (DTPA) and ethylenediamine-tetraacetic acid (EDTA) and similar molecules. Alternatively, other forms of detectable labels can be used to render the labeled molecule detectable.

Screening methods for detection, isolation, or identification of molecules or combinations of molecules that inhibit interaction of Hec1 protein with other proteins, including Hint1 protein and Nek2 protein, or which prevent the modification of Hec1 protein by the action of Hint1 protein or Nek2 protein, or the action of other proteins recruited by Hint1 protein or Nek2 protein, are contemplated as an aspect of the present invention. Such screening methods can include detection, isolation, or identification of molecules or combinations of molecules by contacting the specified Hec1 protein, Nek2 protein, Hint1 protein, or any combination thereof with the molecule or combination of molecules and determining a change in the function or activity of the specified protein. The specified proteins can be in tissues, in cells, in cell lysate or extracts, or can be isolated. For example, cells can be contacted with a potential therapeutic agent. Cells so treated and used in the practice of the screening method can be cultured cells, isolated cells, cells in a tissue, or cells in an organism. In certain embodiments, the invention features a method of identifying a molecule or combination of molecules that interfere with the function of Hec1 protein, Nek2 protein, and/or Hint1 protein and that inhibits cell proliferation, comprising: contacting a sample comprising cells with the molecule or combination of molecules; and measuring the amount of cell proliferation, cell cycle progression, cell cycle arrest, or apoptosis in the sample exposed to the molecule or combination of molecules, whereby a decrease in cell proliferation, a decrease in cell cycle progression, an increase in cell cycle arrest, or an increase in apoptosis in the sample comprising proliferating cells exposed to the molecule or combination of molecules, relative to the amount of proliferation, cell cycle progression, cell cycle arrest, or apoptosis in a sample comprising proliferating cells not contacted with the molecule or combination of molecules, identifies a molecule or combination of molecules that inhibits proliferation of the cells.

In other screening methods, activity of potential or putative molecules that interference with Hec1, Nek2, and/or Hint1 activity, or combinations of such molecules, can be monitored ex vivo. In the practice of these screening methods, the level of specified protein function can be monitored by direct determination of interaction between the specified protein and another protein or other proteins. Determination of the level of interaction can be monitored directly by measurement of labeled proteins binding to immobilized binding partners or by co-immunoprecipitation of binding partners using antibodies of defined specificity or by any other method as is known to those of skill in the art that can be used to directly monitor protein-protein interactions in solution. Alternatively, the level of interaction can be monitored indirectly by detection and quantification of the level or degree of modification of a specified protein wherein the level or degree of modification is an indicator of levels of interaction. In particular, the character or level of phosphorylation can be used to ascertain the level or degree of interaction that occurs. For example, the level of phosphorylation of Hec1 protein, particularly at residue 165, can be used to determine the relative presence of interactions between Hec1 protein and Nek2 protein. Other screening methods described in the Examples, such as use of the two-hybrid system, are particularly contemplated as methods that can be used to identify compounds that can be used to block interactions between Hec1 and other proteins and that can be used to inhibit cell proliferation.

Compounds or molecules identified by the use of the screening methods of the invention are contemplated as a further aspect of the invention. Particular examples of these compounds are shown in the Figures of the present disclosure. These include IBT4282, IBT6432, IBT11830, IBT12008, IBT13131, IBT14664, and IBTG15154. Modifications or derivatizations of these compounds to generate mimetics are also contemplated. Any mimetics so generated are then tested for their ability to effect Hec1 protein, Nek2 protein, or Hint1 protein function.

Methods of treating or preventing disease are also contemplated as an aspect of the present invention. For example, the invention encompasses a method of treating or preventing a disease involving cell hyperproliferation in a subject, comprising administering to the subject a molecule, wherein the molecule affects the function of a Hec1 protein, a Nek2 protein, a Hint1 protein, or a combination thereof, thereby reducing proliferation of cells in the subject. In particular aspects, the method of treating or preventing a proliferative disease will comprise blocking interaction between Hec1 protein and at least one further protein, thereby lessening proliferation. Alternatively, the method can comprise blocking interactions of Hec1 with two or more further proteins. In other embodiments, the method can comprises blocking interactions with fewer than 7, 6, 5, 4, 3, or 2 proteins or with more than 2, 3, 4, 5, or 6 proteins. The further protein(s) can be selected from a group of proteins that include Nek2 protein and Hint1 protein or functional homologs thereof.

In certain aspects of the methods of treating or preventing disease, the method includes reducing (i.e., partially or completely inhibiting) phosphorylation of residue 165 of Hec1 protein, or a corresponding functional residue of a homolog of Hec1 protein, thereby lessening proliferation. The reduction/inhibition can be greater than 5%, 10%, 20%, 30%, 40%, 50%, 60%, 70%, 80%, 90%, 95%, 97%, or 99% from the level of phosphorylation that normally occurs in either the natural state or in the disease state. The reduction of phosphorylation can be achieved by partially or fully inhibiting (e.g., blocking, weakening, or lessening) the interaction of Hec1 protein or a homolog thereof with a protein that acts as a kinase.

The reduction of interaction between Hec1 protein and further proteins can be effected by the presence of small molecule drugs, antibodies, reduced levels of Hec1 and further proteins, or a combination thereof. Small molecules that can be used include those described herein and those that can be identified by the process and methods described herein for the identification of drugs having the ability to block interactions, thereby lessening cell proliferation, or for reducing the level of phosphorylation of Hec1 protein, thereby lessening cell proliferation.

The methods of the invention can be used to treat diseases of cell hyperproliferation. One broad category of such diseases is cancer. Cancers can be carcinomas, e.g., but not limited to, acinar carcinoma, adenocystic carcinoma, adenosquamous carcinoma, adnexal carcinoma, alveolar carcinoma, apocrine carcinoma, basal cell carcinoma, bladder carcinoma, breast carcinoma, bronchioloalveolar carcinoma, bronchogenic carcinoma, cervical carcinoma, colon carcinoma, cholangiocellular carcinoma, chorionic carcinoma, clear cell carcinoma, colloid carcinoma, cribriform carcinoma, ductal carcinoma, embryonal carcinoma, carcinoma en cuirasse, endometroid carcinoma, epidermoid carcinoma, esophageal carcinoma, carcinoma ex pleomorphic adenoma, follicular carcinoma of thyroid gland, gastric carcinoma, hepatocellular carcinoma, carcinoma in situ, intraductal carcinoma, Hurthle cell carcinoma, inflammatory carcinoma of the breast, large cell carcinoma, lung carcinoma, invasive lobular carcinoma, lobular carcinoma, medullary carcinoma, meningeal carcinoma, Merkel cell carcinoma, mucinous carcinoma, mucoepidermoid carcinoma, nasopharyngeal carcinoma, non-small cell carcinoma, oat cell carcinoma, pancreatic carcinoma, papillary carcinoma, prostate carcinoma, renal cell carcinoma, scirrhous carcinoma, sebaceous carcinoma, carcinoma simplex, signet-ring cell carcinoma, small cell carcinoma, spindle cell carcinoma, squamous cell carcinoma, terminal duct carcinoma, transitional cell carcinoma, tubular carcinoma, and verrucous carcinoma.

Cancers can also be sarcomas, e.g., but not limited to, alveolar soft part sarcoma, ameloblastic sarcoma, botryoid sarcoma, clear cell sarcoma of kidney, endometrial stromal sarcoma, Ewing's sarcoma, giant cell sarcoma, hemangioendothelial sarcoma, immunoblastic sarcoma of B cells, immunoblastic sarcoma of T cells, Kaposi's sarcoma, Kupffer cell sarcoma, osteogenic sarcoma, pseudo-Kaposi sarcoma, reticulum cell sarcoma, Rous sarcoma, soft tissue sarcoma, and spindle cell sarcoma. Other cancers that can be treated by the methods of the invention include, but are not limited to, retinoblastoma, neuroblastoma, and glioblastoma.

The methods of the invention can also be used to treat hyperproliferative diseases or conditions that are not cancers, e.g., diseases or conditions involving stenosis. For example, the methods of the invention can be used to treat or prevent re-stenosis that occurs in a blood vessel, such as, but not limited to, that which occurs following balloon angioplasty or other treatments that cause injury to the blood vessels. Other examples of stenosis that can be treated by the methods of the present invention include, but are not limited to, aortic stenosis, hypertrophic pyloric stenosis, infantile hypertrophic gastric stenosis, mitral stenosis, pulmonary stenosis, pyloric stenosis, subaortic stenosis, renal artery stenosis, and tricuspid stenosis.

Methods of Administration

The HEC1 inhibitors of the invention and compounds identified using any of the methods disclosed herein may be administered to subjects with a pharmaceutically acceptable diluent, carrier, or excipient, in unit dosage form. By "pharmaceutically acceptable" is meant a material that is not biologically or otherwise undesirable, i.e., the material may be administered to an individual along with a HEC1 inhibitor without causing any undesirable biological effects or interacting in a deleterious manner with any of the components of the pharmaceutical composition in which it is contained. Conventional pharmaceutical practice may be employed to provide suitable formulations or compositions to administer such compositions to subjects. Any appropriate route of administration may be employed, for example, but not limited to, intravenous, parenteral, transcutaneous, subcutaneous, intramuscular, intracranial, intraorbital, ophthalmic, intraventricular, intracapsular, intraspinal, intracisternal, intraperitoneal, intranasal, intrarectal, intravaginal, aerosol, or oral administration. Therapeutic formulations may be in the form of liquid solutions or suspensions; for oral administration, formulations may be in the form of tablets or capsules; for intranasal formulations, in the form of powders, nasal drops, or aerosols; for intravaginal formulations, vaginal creams, suppositories, or pessaries; for transdermal formulations, in the form of creams or distributed onto patches to be applied to the skin; for dental formulations, in the form of mouthwashes or toothpastes.

Methods well known in the art for making formulations are found in, for example, Remington: The Science and Practice of Pharmacy (19th ed.) ed. A. R. Gennaro, Mack Publishing Company, Easton, Pa. 1995. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Dosage

The HEC1 inhibitors of the invention may be administered to a subject in an amount sufficient to partially or fully inhibit HEC1 activity (e.g., the role of HEC1 in ensuring faithful chromosome segregation, e.g., by inhibiting HEC1 phosphorylation or by inhibiting HEC1 interaction with a protein involved in chromosome segregation), or to treat, prevent, or inhibit a disease or condition of cellular hyperproliferation in a subject in need of such treatment, prevention, or inhibition. One of ordinary skill in the art will understand that optimal dosages used will vary according to the individual being treated, the particular compound being used, and the chosen route of administration. The optimal dosage will also vary among individuals on the basis of age, size, weight, gender, and physical condition. Methods for determining optimum dosages are described, for example, in Remington: The Science and Practice of Pharmacy (19th ed.) ed. A. R. Gennaro, Mack Publishing Company, Easton, Pa. 1995.

The amount of active ingredient that may be combined with a carrier material to produce a single dosage form will vary depending upon the disease treated, the animal species, and the particular mode of administration. A therapeutically effective amount may be determined by routine experimentation, as will be understood by one of ordinary skill in the art. In general, about 50 µg to about 500 mg of HEC1 inhibitory compound is administered per day, although other dosages can be used as appropriate. For example, for treatment of humans, a compound of the invention could be administered in an amount ranging from approximately 0.001 to 10 mg/kg of body weight. The compounds can be administered daily (e.g., one to four times per day) or can be administered weekly, monthly, or sporadically, as is well known in the art.

Efficacy

The efficacy of administration of a particular dose of a HEC1 inhibitor can be determined by evaluating the particular aspects of the medical history, signs, symptoms, and objective laboratory tests that are known to be useful in evaluating the status of a subject requiring treatment, prevention, or inhibition of a disease or condition involving cellular hyperproliferation, e.g., cancer or a stenosis. These signs, symptoms, and objective laboratory tests will vary, depending upon the particular disease or condition being treated or prevented, as will be known to any clinician who treats such subjects or to a researcher conducting experimentation in this field. For example, if, based on a comparison with an appropriate control group and knowledge of the normal progression of disease in the general population or the particular individual: 1) a subject's frequency or severity of recurrences is shown to be improved, 2) the progression of the disease is shown to be stabilized or delayed, or 3) the need for use of other medications for treating the condition or disease is lessened or obviated, then a particular treatment will be considered efficacious.

In a specific example, in using a HEC1 inhibitor of the present invention to treat a tumor, a slowing or partial or complete inhibition of tumor growth or metastases, or even shrinkage of the tumor, are indications that the treatment is efficacious. Similarly, in using a HEC1 inhibitor to treat a stenosis, if the progression of the stenosis is slowed, partially or completely inhibited or arrested, or even reversed, these are indications that the treatment is efficacious.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. The Examples included herein are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE I

Chromosome Segregation Requires Phosphorylation of Hec1 BY Nek2

A) Experimental Procedures

Cell Culture, Synchronization.

Human bladder carcinoma T24 cells (American Type Tissue Collection, Rockville, Md.) grown in DMEM/10% FBS were synchronized at G1 by density arrest and then released at time zero by replating in DMEM-10% FCS at a density of $2 \times 10^6$ cells per 10 cm-plate. At various time points thereafter (18 h for G1/S, 22 h for S, 32 h for G2), the cells were harvested. To obtain a cell population enriched in M phase, nocodazole (0.4 µg/ml) was added to the culture medium for 8 h prior to harvest (Chen, Y., et al. *Cancer Res.* 56, 3168-3172, 1996).

Yeast Strains, Reagents and Media.

Yeast strains are described in Table 1. Strains used in this study were grown in complete medium (YPD: 1% yeast extract, 2% peptone, and 2% dextrose) or in supplemented minimal medium (SMM) with appropriate amino acids missing. The chemicals and medium components were purchased from Sigma-Aldrich (St. Louis, Mo.) and BD Industries (Franklin Lakes, N.J.).

mM dithiothreotol). Clarified yeast cell lysates were then used for co-immunoprecipitation by anti-Hec1 mAb 9G3 or anti-scHec1 polyclonal antisera as described above. After 4 hours incubation with antibodies and protein A sepharose beads, the beads were collected and washed extensively with lysis buffer, then boiled in SDS-loading buffer. After immunoblotting to Immobilon-P membrane (Millipore, Bedford, Ma.), the blots were probed with anti-scHec1 antibodies,

TABLE I

Yeast strains and genotypes

| Strain | Genotype | Source |
| --- | --- | --- |
| YPH499 | Mat a ura3-52 lys2-801 ade2-101 trp1-Δ63 his3-Δ200 leu2-Δ1 | P. Hieter |
| WHL101 | Mat a ura3-52 lys2-801 ade2-101 trp1-Δ63 his3-Δ200 leu2-Δ1 schec1Δ::URA3 hsHEC1 (YcpPA- HSHEC1::TRP1) | W-H. Lee |
| WHL-SE | Mat a ura3-52 lys2-801 ade2-101 trp1-Δ63 his3-Δ200 leu2-Δ1 schec1Δ::URA3 hsHEC1(YcpPA- hshec1S165E::TRP1) | This study |
| WHL103 | Mat a ura3-52 lys2-801 ade2-101 trp1-Δ63 his3-Δ200 leu2-Δ1 schec1Δ::URA3 scHEC1 (YcpPA- scHEC1::TRP1) | W-H. Lee |
| WHL-S201 | Mat a ura3-52 lys2-801 ade2-101 trp1-Δ63 his3-Δ200 leu2-Δ1 schec1Δ::URA3 scHEC1 (YcpPA- scHEC1S201E::TRP1) | This study |
| WHL6001 | Mat a ura3-52 lys2-801 ade2-101 trp1-Δ63 his3-Δ200 leu2-Δ1 scnec2Δ::URA3 Ycp::LEU2 | This study |
| WHL6009 | Mat a ura3-52 lys2-801 ade2-101 trp1-Δ63 his3-Δ200 leu2-Δ1 scnec2Δ::URA3 scNek2(Ycp- scNek2D55G::LEU2) | This study |
| WHL6010 | Mat a ura3-52 lys2-801 ade2-101 trp1-Δ63 his3-Δ200 leu2-Δ1 scnec2Δ::URA3 NEK2(Ycp- nek2E38G::TRP1) | This study |
| WHL6012 | Mat a ura3-52 lys2-801 ade2-101 trp1-Δ63 his3-Δ200 leu2-Δ1 scNek2(Ycp- scNek2D55G::LEU2) schec1Δ::URA3 hsHEC1 (YcpPA-HSHEC1::TRP1) | This study |
| WHL6013 | Mat a ura3-52 lys2-801 ade2-101 trp1-Δ63 his3-Δ200 leu2-Δ1 scnek2Δ::URA3 scNek2(Ycp- scNek2D55G::LEU)(Ycp::TRP1) | This study |
| WHL6014 | Mat a ura3-52 lys2-801 ade2-101 trp1-Δ63 his3-Δ200 leu2-Δ1 scnek2Δ::URA3 scnek2(Ycp- scNek2D55G::LEU) KIN3(Ycp-scNek2::TRP1) | This study |
| WHL6015 | Mat a ura3-52 lys2-801 ade2-101 trp1-Δ63 his3-Δ200 leu2-Δ1 scnek2Δ::URA3 scnek2(Ycp- scNek2D55G::LEU) NEK2(Ycp-NEK2::TRP1) | This study |
| YPH1017 | Mat α ura3-52 lys2-801 ade2-101 trp1-Δ63 his3-Δ200 leu2-Δ1 (CFIII HIS3 SUP11) | P. Hieter |
| WHL2003 | Mat a/χ lys2-801/lys2-801 ade2-101/ade2-101 leu2-Δ1/leu2-Δ1 scHEC1/scHEC1 (CFIII TRP1 SUP11) | W-H. Lee |
| WHL4003 | Mat a/χ lys2-801/lys2-801 ura3-52/ura3-52 ade2-101/ade2-101 trp1- Δ63/trp1-Δ63 his3-Δ200/his3-Δ200 leu2-Δ1/leu2-Δ1 schec1Δ::URA3/schec1Δ::URA3 hsHEC1 (YcpPA-HSHEC1-TRP1) (CFIII HIS3 SUP11) | This study |
| WHL4001 | Mat a/χ lys2-801/lys2-801 ura3-52/ura3-52 ade2-101/ade2-101 trp1-Δ63/trp1-Δ63 his3-Δ200/his3-Δ200 leu2-Δ1/leu2-Δ1 schec1Δ::URA3/schec1Δ::URA3 hsHEC1 (YcpPA-HSHEC1::TRP1) (CFIII HIS3 SUP11) hshec 1S165E (YcpPA-hshec1S165E::TRP1) | This study |
| WHL6502 | Mat a/χ lys2-801/lys2-801 ade2-101/ade2-101 leu2-Δ1/leu2-Δ1 scHEC1/scHEC1 (CFIII TRP1 SUP11) scnek2Δ::URA3/scnek2Δ::URA3 (CFIII TRP1 SUP11) | This study |

Immunoprecipitation and Western Blot Analysis.

T24 cells resuspended in ice-cold Lysis 250 buffer (50 mM Tris-Hcl, pH 7.4, 250 mM NaCl, 5 mM EDTA, 0.1% Nonidet p40, 50 mM NaF, 1 mM phenylmethylsulfonyl fluoride) were subjected to three freeze/thaw cycles (liquid nitrogen/37° C.), then centrifuged at 14,000 rpm for 2 min at room temperature. The supernatants were used for immunoprecipitation as described (Chen, P.-L., et al. Cell 58, 1193-1198, 1989). Briefly, anti-Hec1 antibody mAb 9G3 (1 μg) or mouse polyclonal anti-Nek2 antiserum (1 μl) was added to each supernatant. After a one-hour incubation, protein-A sepharose beads were added and incubation continued for another hour. Beads were collected, washed five times with lysis buffer containing hypertonic NaCl, and then boiled in SDS-loading buffer for immunoblot analysis as described (Chen, P.-L., et al. Cell 58, 1193-1198, 1989). For the co-immunoprecipitation experiments from yeast cells, yeast cell lysate was prepared as described (Zheng, L., et al. Mol Cell Biol 19, 5417-5428, 1999). Briefly, yeast cells were collected by centrifugation and washed with cold distilled $H_2O$ twice. Cells were then broken by glass beads in lysis buffer (50 mM Tris, pH 7.5, 10 mM $MgSO_4$, 1 mM EDTA, 10 mM KOAc, 1 anti-Hec1 mAb 9G3, or anti-Kin3 antibodies. All the immunoblots but one were developed by 5-bromo,4-chloro,3-indolylphosphate (BCIP)/nitroblue tetrazolium (NBT) substrate for alkaline phosphatase conjugated anti-mouse antibodies. Horseradish peroxidase conjugated protein A was used to detect anti-Kin3 antibodies and blots using that antibody were developed using an ECL chemiluminescence kit (AmershamPharmacia, Piscataway, N.J.), according to the manufacturer's instructions.

Metabolic Labeling.

T24 cells grown in DMEM/10% FCS were synchronized at G1 by density arrest and then released at time zero by replating in DMEM-10% FCS at a density of $2\times10^6$ cells per 10 cm-plate. At various time points thereafter (18 h for G1/S, 22 h for S, 32 h for G2), the cells were metabolically labeled with 100 μCi/ml $^{32}$P-phosphoric acid (ICN, Costa Mesa, Calif.) for 3 hours and harvested for immunoprecipitation with mAb 9G3 anti-Hec1 antibodies as described above.

Colony Sectoring Assay.

Chromosome segregation errors were measured by colony sectoring assay as described (Zheng, L., et al. Mol Cell Biol 19, 5417-5428, 1999; Koshland, D., and Hieter, P. Methods

*Enzymol* 155, 351-372, 1987), except that adenine was added at a concentration of 6 µg/ml instead of 30 µg/ml.

Purification of His Tagged Hec1 Protein.

cDNA encoding full length Hec1 was digested with XhoI and fused in-frame to 6×His at the N-terminus and expressed in *E. coli* using the PET expression system (Studier, F. W., and Moffatt, B. A. (1986) *J Mol Biol* 189, 113-130). After induction with 0.1 mM isopropylthiogalactoside, cells were lysed and clarified by centrifugation. The clarified total soluble cellular protein was passed through DEAE. Sepharose column (Amersham Biosciences, Piscataway, N.J.). The flow-through from the DEAE-Sepharose column was passed through an SP-Sepharose column (Amersham) and eluted with a 100 to 750 mM NaCl gradient. His-Hec1 eluted at fractions between 200 and 300 mM NaCl. The fractions from the SP sepharose column were loaded onto a Ni-Sepharose column (Amersham) and eluted with 60 mM imidozole. The Hec1 protein was fractionated by Sephadex 300 to obtain purified protein.

Expression of His-Tagged Nek2 in a Baculovirus System.

Full-length Nek2 was fused in-frame to 6×His and expressed in a baculovirus system as described (Smith, G. E., Summers, M. D., and Fraser, M. J. (1983) *Mol Cell Biol* 3, 2156-2165). 36 hours after infection, the infected sf9 cells were lysed and immunoprecipitated with anti-Nek2 antisera. The resulting immune complexes were used in kinase assays.

In Vitro Kinase Assay.

Immunoprecipitated recombinant Nek2 was washed with Lysis 250 buffer 5 times, followed by washing twice with Tris-buffered saline (10 mM Tris-HCl, pH 7.4, 20 mM NaCl) and once with distilled $H_2O$. The kinase reactions were carried out for 20 min at 37° C. in Nek2 kinase buffer (0.5 M Hepes, pH 7.5, 50 mM $MnCl_2$, 50 mM NaF, 50 mM β-glycerol phosphate, 10 µM okadaic acid, 10 µg/ml heparin sulfate, 40 µM ATP, and 10 mM dithiothreotol) supplemented with 10 µCi γ-$^{32}$P ATP. Purified Hec1 proteins (5 µg) were added to the kinase reactions as described (Fry, A. M., et al. (1995) *J Biol Chem* 270, 12899-12905). Kinase reactions were stopped by adding 2×SDS sample buffer and proteins were separated by SDS-PAGE. The resulting gel was dried and autoradiographed.

Phosphoamino Acid Analysis.

T24 cells were labeled with $^{32}$P-orthophosphoric acid for two hours, followed by immunoprecipitation with mAb 9G3 anti-Hec1 antibody. Immune complexes were separated by SDS-PAGE and transferred to Immobilon-P membrane. Phosphoamino acid analysis was performed as described (Boyle, W. J., et al. (1991) *Methods In Enzymnology* 201, 110-152).

Antibody Production.

For production of anti-Nek2 antibody, cDNA encoding a.a. 235-399 of Nek2 was fused to glutathione S-transferase (GST) in-frame. Purified GST-Nek2 fusion protein was used as antigen to immunize a mouse to produce mouse polyclonal anti-Nek2 anti-sera. For the anti-Kin3 antibody, cDNA encoding full-length Kin3 was fused to GST in-frame; the fusion protein was purified and used as an antigen. Anti-Hec1 and anti-scHec1 antibodies have been described (Chen, Y., et al. (1997) *Mol. Cell. Biol.* 17, 6049-6056; Zheng, L., et al. (1999) *Mol Cell Biol* 19, 5417-5428). For anti-phosphorylated Hec1 antibody, a synthetic phosphopeptide (A439, FIG. 3A) was coupled to keyhole limpet hemacyanin (KLH) and used as antigen.

B) Results

HEC1 is a Serine Phosphoprotein and its Phosphorylatlon is Cell Cycle Dependent.

Figure 1B:
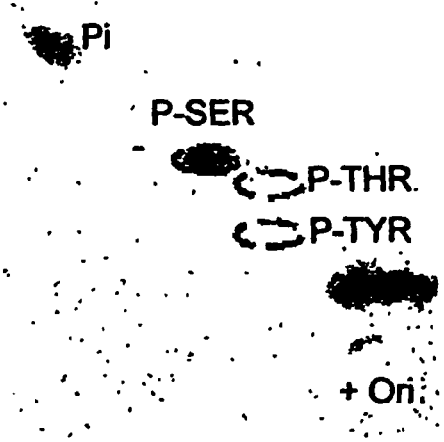
Figure 1C:
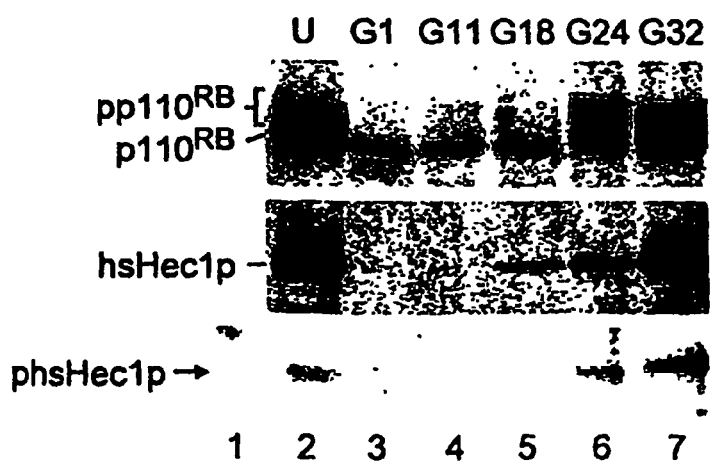

To explore a potential mechanism by which Hec1 is regulated, we tested whether Hec1 is modified by phosphorylation. T24 cells were labeled with either $^{35}$S-methionine or $^{32}$P-orthophosphate and lysed. The lysates were immunoprecipitated with polyclonal anti-Hec1 serum, monoclonal anti-Hec1 antibodies (mAb9G3), or pre-immune serum, then separated by SDS-PAGE. The 76 kDa Hec1 protein recognized by both polyclonal and mAb 9G3 antibodies was labeled by $^{32}$p (FIG. 1A, lanes 5 and 6), showing Hec1 to be a phosphoprotein. Phospho-amino acid analysis showed Hec1 to be phosphorylated only on serine residues (FIG. 1B). To determine the cell cycle dependence of Hec1 phosphorylation, T24 cells released from density arrest at G0 phase for different periods of time were labeled with $^{32}$P-orthophosphate and analyzed. The phosphorylation of Hec1 began during time periods corresponding to S phase and was most prominent during M phase (FIG. 1C). These results showed Hec1 to be phosphorylated on serine residues by a cell cycle-regulated serine kinase.

Hec1 Binds to Nek2 Specifically at G2/M Phase.

A candidate kinase for phosphorylating Hec1 is Nek2, which we found in a yeast two-hybrid screen to interact specifically with Hec1 (Chen, Y., et al. (1997) *Mol. Cell. Biol.* 17, 6049-6056). The binding of Hec1 with Nek2 was further established using GST pull down assays (FIG. 2A). In vitro translated Nek2 interacted with the carboxyl terminal portion of Hec1 (a.a. 251-618). Using Hec1 deletion constructs and yeast two-hybrid assays, we found that Hec1 interacts with Nek2 via the first (a.a. 251-431) or second (a.a. 361-547) coiled-coil domain (FIG. 2B).

To determine the cell cycle specificity of the Hec1-Nek2 interaction in living cells, T24 cells released from density arrest at G0 phase were collected at various subsequent time points. Proteins from cell lysates were immunoprecipitated with either anti-Nek2 serum or with mAb 9G3, which recognizes Hec1. The expression of both Hec 1 and Nek2 was regulated during progression of the cell cycle (FIG. 2C). Co-immunoprecipitation of Nek2 and Hec1 occurred specifically during G2 and M phases (FIG. 2C, lanes 5 and 6). The initiation of Hec1 phosphorylation (FIG. 2C, G24, lane 6) corresponded to the same time period during Nek2 was most abundant (FIG. 2C, lane 4), suggesting that Nek2 phosphorylates Hec1 in vivo during G2/M phase.

Phosphorylation of Hec1 on Serine 165 in Vivo.

We noted that Hec1 has a potential phophorylation site at serine 165 for both NimA and Nek2 (FIG. 3A). To test whether Ser 165 of Hec1 is the authentic site phosphorylated by Nek2, an antibody specifically recognizing a synthesized Hec1 phosphopeptide (FIG. 3A) was generated and used to examine the expression of phosphorylated Hec1 (FIG. 3B). Lysates from T24 cells, either from cells synchronized at M phase or from an unsynchronized population, were immunoprecipitated with anti-Hec1 antibodies. The anti-A439 antibody recognized phophorylated form of Hec1, but did not recognize the unphosphorylated form from lysates treated with calf intestine phosphatase (FIG. 3B). In contrast, interaction between Hec1 and mAb 9G3 recognized both phosphorylated and unphosphorylated forms of Hec1, and was not affected by phosphatase treatment (FIG. 3B). The phosphorylated form of Hec1 was detected most abundantly by anti-A439 in the lysates enriched for mitotic cells (FIG. 3C, lane 3). This finding is consistent with the $^{32}$P labeling experiment shown in FIG. 1C, in which the phosphorylated form of Hec1 was most abundant at the G2/M phase. Together the results suggest that Hec1 is phosphorylated on serine 165 in vivo.

Nek2 Phosphorylates Hec1 in Vitro.

Figure 4A:
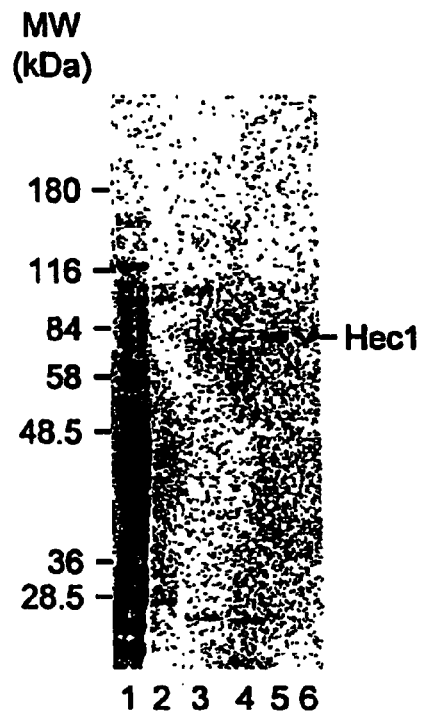
FIG. 4A-4D. Nek2 phosphorylates Hec1 in vitro.
Figure 4B:
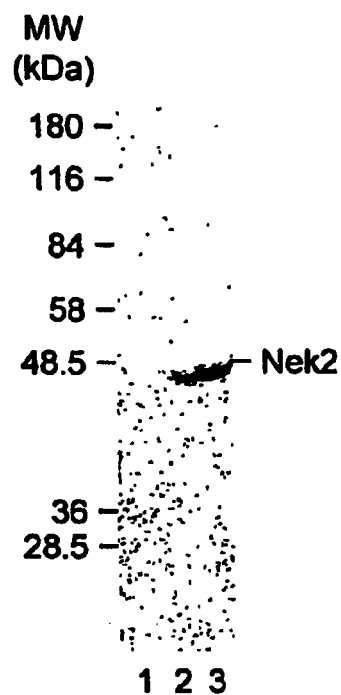
Figure 4C:
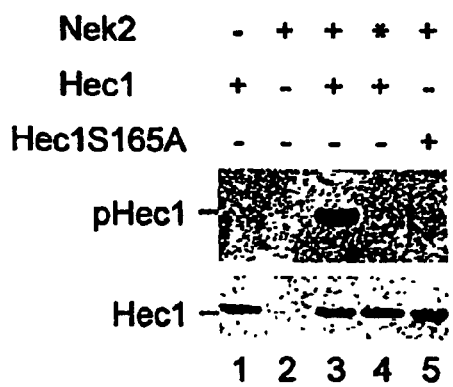
Figure 4D:
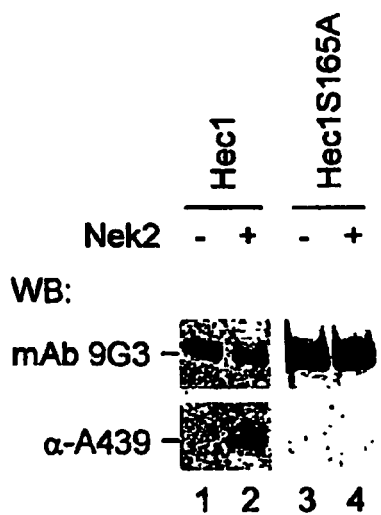

To determine whether Nek2 phosphorylates Hec1 directly, his-tagged, wild-type Hec1 and a specific Hec1 mutant (Hec1 S165A) changing the putative Nek2 phosphorylation site at serine 165 into a neutral amino acid, alanine, were then expressed and purified to near homogeneity using a PET expression system (FIG. 4A). His-tagged Nek2 was expressed in a baculovirus system and immunopurified using anti-Nek2 antibodies (FIG. 4B). Kinase reactions were then performed using purified Hec1 and Hec1S165A mutant as substrates. Nek2 phosphorylated wild-type Hec1 (FIG. 4C, lane 3) but not Hec1S165A (lane 5). Proteins immunoprecipitated by nonspecific, pre-immune antibodies (FIG. 4C, lane 1) or intentionally heat-inactivated Nek2 (FIG. 4C, lane 4) failed to phosphorylate Hec1. Furthermore, anti-A439 recognized the phosphorylated form of Hec1 (FIG. 4D, lane 2), but not the Hec1 S165A mutant even after the kinase reaction (FIG. 4D, lanes 3 and 4). Anti-A439 did not recognize the unphosphorylated form of wild-type Hec1 (FIG. 4D, lane 1). These results confirmed the residue on which Nek2 kinase phosphorylates Hec1 is serine 165.

Yeast Kin3 Shares Similar Properties with Nek2.

Figures 5A, 5D:
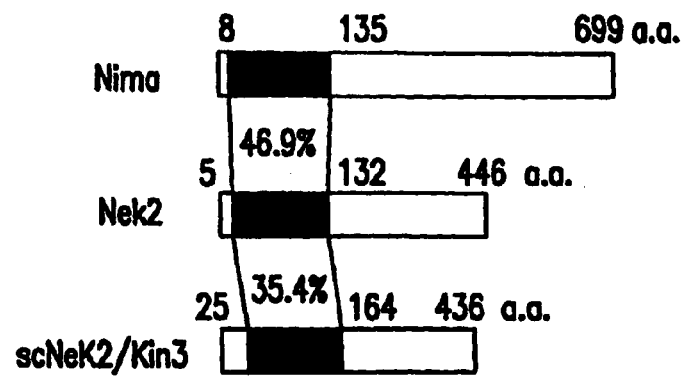
Figure 5C:
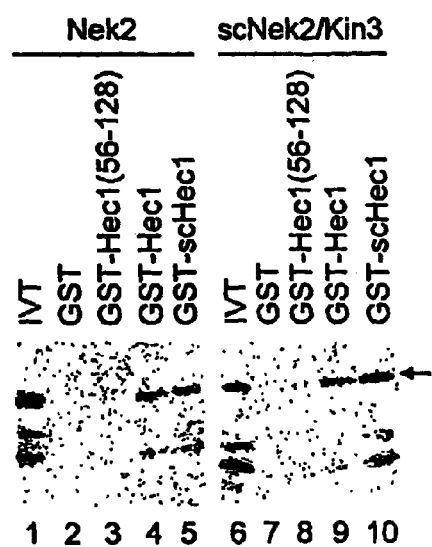

Human Hec1 (hsHec1) has a structural and functional homolog, scHec1/TID3/ndc80/YIO4, in yeast that is required for faithfull chromosome segregation (Zheng, L., et al. (1999) *Mol Cell Biol* 19, 5417-5428). Since Hec1 is specifically phosphorylated at the G2 and M phases, phosphorylation of Hec1 by Nek2 may be critical for chromosome segregation. To address this possibility, yeast model system was employed, because well-established methods are available to assay chromosome segregation (Zheng, L., et al. (2000) *Mol Cell Biol* 20, 3529-3537; Zheng, L., et al. (1999) *Mol Cell Biol* 19, 5417-5428; Koshland, D., and Hieter, P. (1987) *Methods Enzymol* 155, 351-372; Kunkel, T. A. (1985) *Proc Natl Acad Sci USA* 82, 488-492). However, we first needed to identify a Nek2 homolog in yeast that might phosphorylate scHec1. There is an open reading frame in the *S. cerevesiae* genome, KIN3, which encodes a putative protein and could function as a serine/threonine kinase (Barton, A. B., et al. (1992) *Gene* 117, 137-140; Jones, D. G., and Rosamond, J. (1990) *Gene* 90, 87-92). This protein shares relatively high homology (36.4% identity) with NimA and human Nek2 in the catalytic domain (FIG. 5A) and contains a coiled-coil domain in its C-terminal region that is similar to the same domains in the other two proteins (FIG. 5B). To test whether these C-terminal regions share similar abilities to physically interact with hsHec1p or scHec1p, Nek2p and Kin3p were synthesized in vitro for GST pull down assays with both GST-hsHec1 and GST-scHec1. Nek2p and Kin3p can bind both human and yeast Hec1p (FIG. 5C). These results suggested that Kin3 and Nek2 not only share homology at their N-terminal kinase domain sequences, but that they also both have Hec1-binding activity at their C-terminal regions.

Figure 6A:
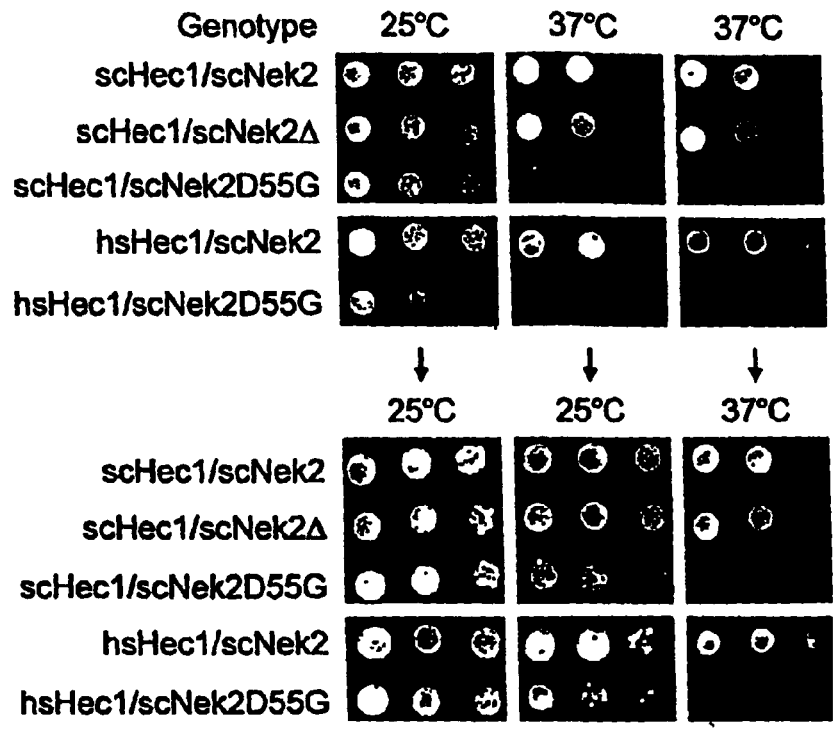
FIG. 6A-6C. Growth properies of the kin3D55G mutant.
Figure 6B:
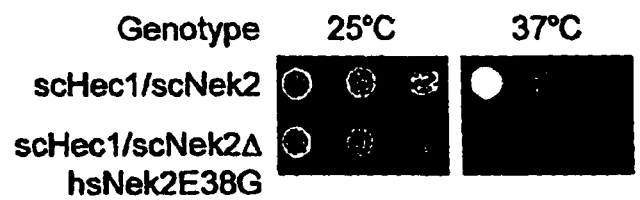
Figure 6C:
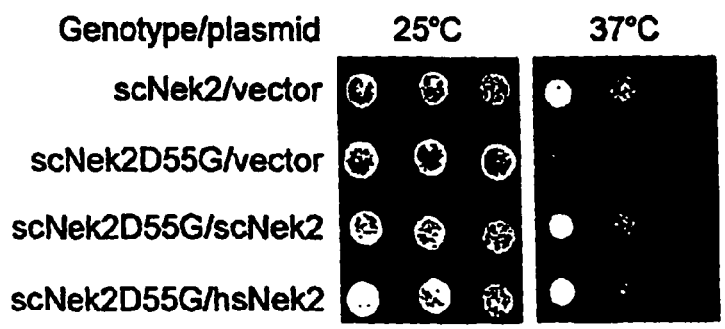

It has been shown that changing glutamic acid 41 of NimA into glycine leads to a temperature sensitive growth phenotype that arrests the cells in the G2 phase at the non-permissive temperature (Osmani, S. A., et al. (1988) *Cell* 52, 241-251; Osmani, S. A., et al. (1987) *J Cell Biol* 104, 1495-1504). Interestingly, similar acidic residues have been found by other researchers to be highly conserved in the other kinases: residue 38 (glutamic acid) in Nek2 (Schultz, S. J., and Nigg, E. A. (1993) *Cell Growth Differ* 4, 821-830), and residue 55 (aspartic acid) in Kin3 (Barton, A. B., et al (1992) *Gene* 117, 137-140; Jones, D. G., and Rosamond, J. (1990) *Gene* 90, 87-92); (FIG. 5D). To test the functional similarity of these key regions among the kinases, glutamic acid 38 of Nek2 and aspartic acid 55 of Kin3 were each changed to glycine. Like the ts nima mutant (Osmani, S. A., et al. (1988) *Cell* 52, 241-251; Osmani, S. A., et al. (1987) *J Cell Biol* 104, 1495-1504), the kin3DS5G mutant (strain WHL 6009) grew at 25° C., arrested at 37° C., and re-entered the cell cycle when shifted back to the 25° C. (FIG. 6A). When the nek2E38G mutant (strain WHL 6010) was introduced into kin3 null cells, growth and propagation of the cells was temperature sensitive as well (FIG. 6B). This ts phenotype was partially suppressed by expression of additional wild-type Kin3 (strain WHL6014) or Nek2 (strain WHL6015) (FIG. 6C). Taken together, these results suggest that Kin3 shares several similar functions with Nek2 and that Kin3 might function as a Nek2 homolog in *S. cerevesiae*.

Temperature-Sensitive Kin3 Mutant Fails to Phosphorylate Hec1 at the Nonpermissive Temperature.

Figure 7A:
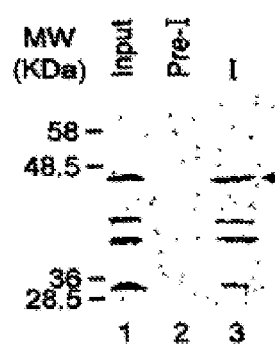
FIG. 7A-7E. Phosphorylation of Hec1 by Nek2.
Figure 7B:
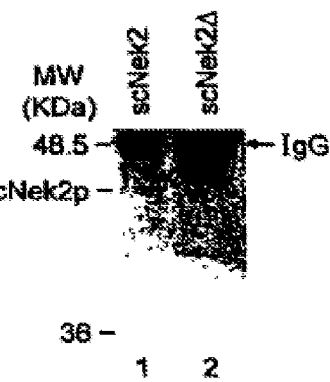
Figure 7C:
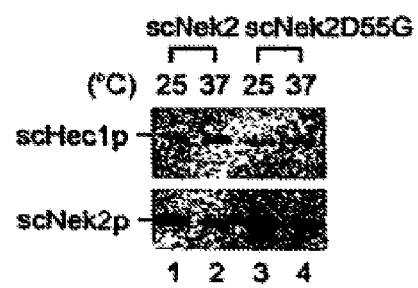
Figure 7D:
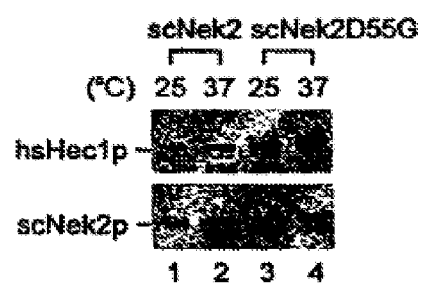
Figure 7E:
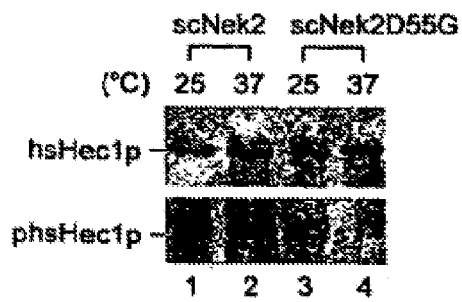

To determine whether kin3D55G may behave in a dominant negative fashion to arrest cells at nonpermissive temperature, we first generated specific antibodies and examined the physical interaction between Kin3p and scHec1p or Kin3p and hsHec1p using co-immunoprecipitation (FIGS. 7A & B). In cells carrying the kin3D55G mutant, the interaction between Kin3p and scHec1p (WHL 6009) or Kin3p and hsHec1p (WHL 6012) (FIGS. 7C & D) was intact, as it was in wild-type Kin3 cells (YPH 499 and WHL01) (FIGS. 7C & D). Moreover, the phosphorylation of hsHec1 on serine 165 was detected by anti-A439 in both wild-type (WHL101) and kin3D55G mutant cells (WHL6012) at the permissive temperature, but not in kin3D55G mutant cells at the nonpermissive temperature (FIG. 7E). These results suggest that phosphorylation of Hec1 by Kin3p is essential for cells to continue cycling. Kin3D55G thus appears indeed to be a dominant negative mutant: it can bind to Hec1 but cannot phosphorylate it.

Phosphorylation of Hec1 Serine 165 is Critical for its Function in Chromosome Segregation.

Figures 8A, 8C:
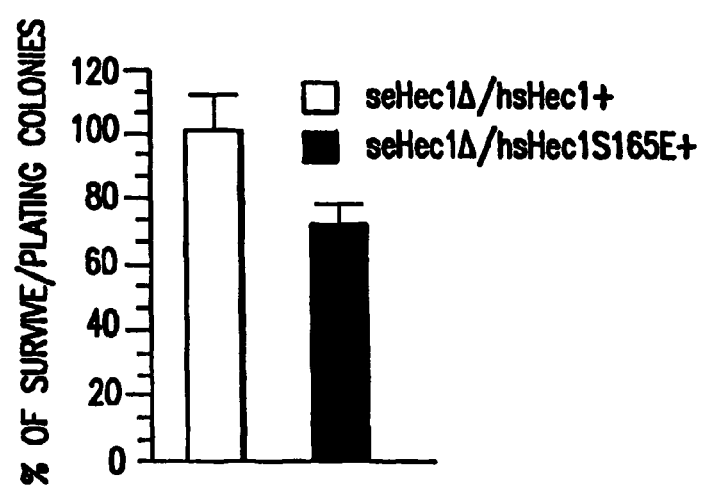
FIG. 8A-8C. Phosphorylation of Hec1 by Nek2 is critical for yeast survival.
Figure 8B:
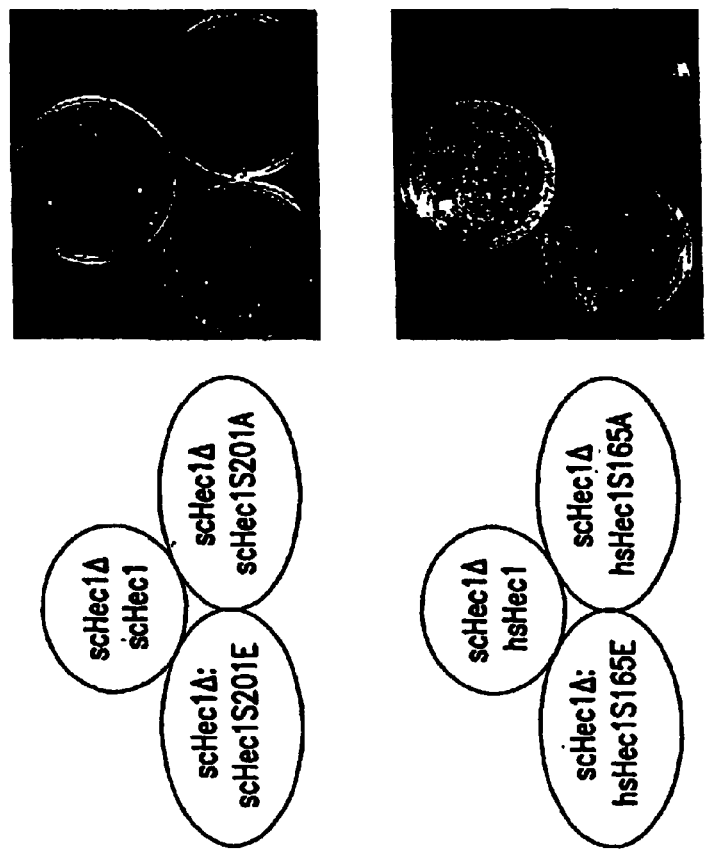

To examine whether the phosphorylation of Hec1 on serine 165 is important for Hec1 to function, yeast strains containing specific Hec1 mutations were created. The homolog of human Hec1 in *S. cerevesiae* (scHec1/TID3/ndc80/YIO4) has been characterized extensively and shown, like its mammalian counterpart, to be essential for chromosome segregation and yeast survival. Furthermore, human Hec1 (hsHec1) can complement the essential functions of scHec1. Two mutant constructs were created: hsHec1S165A, substituting a the neutral amino acid alanine for serine, and hsHec1S165A, substituting glutamic acid for serine to mimic the negative charge created by serine phosphorylation (FIG. 8A). To test whether these Hec1 mutants could complement scHec1 deficiency, they were introduced into the scHec1 null yeast strain. HsHec1S165E was able to rescue yeast deficient in scHec1 but the hsHec1S165A mutant was not (FIG. 8B). These results suggest that phosphorylation of serine 165 is important for the function of Hec1.

To determine whether substituting glutamic acid for serine 165 in Hec1 could rescue all essential functions of Hec1 in yeast, the plating efficiency and chromosome segregation were examined in scHec1 null yeast rescued by either wild-type Hec1 (strain WHL 101) or Hec1S165E (strain WHL-SE). The plating efficiency of WHL-SE was only 75% of the efficiency for the wild-type strain WHL101 (FIG. 8C). This result suggested that the HecS165E was not fully functional in allowing faithful mitosis. To address this possibility, colony sectoring assays were performed in the two yeast strains to monitor chromosome segregation. Yeast cells rescued by the hsHec1S165E (strain WHL 4001) were ten times more prone to segregation errors, especially chromosome loss (1:0) events, compared to cells rescued by wild-type hsHec1 (strain WHL4003) (Table 2). Yeast cells lacking Kin3, although viable, appear to have subtle errors in chromosomal segregation. To test this possibility, kin3 null cells (strain WHL6502) were examined by colony sectoring assays. They were found to have 50-fold higher rates of errors of chromosomal losses (1:0 events) and 6-fold higher rates of non-disjunction (2:0 events) (Table 2). Taken together, the results suggest that precisely regulated phosphorylation of Hec1 by Nek2 is critical for accurate chromosome segregation during mitosis.

Figure 11A:
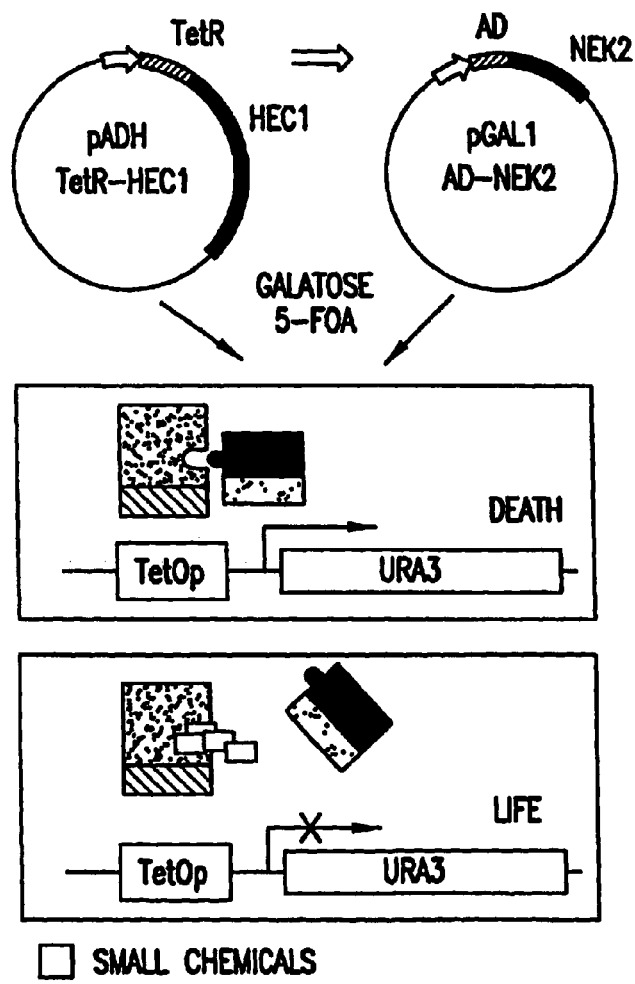
FIG. 11A. Schematic diagram of the inducible reverse two-hybrid system designed to detect small molecules that disrupt interactions between Hec1 and Nek2. The TetR-Hec1 fusion protein (TetR/Hec1) is constitutively expressed while the GAL1 promoter regulates expression of the Nek2-activation domain fusion protein (AD/Nek2). After Gal induction, the AD-Nek2 fusion protein is expressed and forms a complex with TetR/Hec1. Their association in turn induces the synthesis of the URA3 gene product, which metabolizes 5FOA into products that will result in cell death. If the small molecules disrupt TetR/Hec1/AD/Nek2 interactions, URA3 expression is inhibited allowing cells to grow.
Figure 11B:
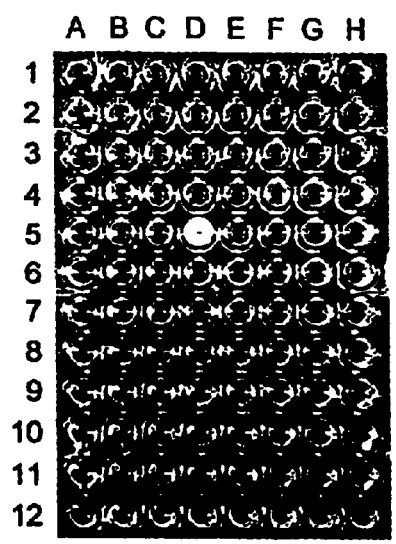
FIG. 11B. Identification of a compound that specifically interferes with the interaction between Hec1 and Nek2 as detected in the reverse two-hybrid system. Yeast were inoculated at density of 0.01 (OD600 reading) in 96-well plates in the synthetic medium containing 2% galactose, 2% raffinose and 0.09% 5FOA, in the presence of the tested compound at a concentration of 10 µM. The yeast cultures were allowed to grow at 30° C. for three days. The well D5 indicates yeast growth.

Hec1 and Nek2. In this system, a TetR (tetracycline regulator)-Hec1 fusion protein (TetR/Hec1) is expressed constitutively, while the expression of a Nek2-B42 Activation Domain fusion protein (AD/Nek2) is rendered galactose-inducible by the GAL1 promoter as illustrated in FIG. 11A-11B. The association of TetR/Hec1 and AD/Nek2 forms an active transcription factor that induces the synthesis of URA3, which is driven by a promoter bearing six copies of the tet operator site. URA3 protein converts 5-Fluoroorotic

TABLE II

Increased chromosome segregation errors Yeast cells null for scHec1 and rescued by the hsHec1S165E mutant (strain WHL4001) were susceptible to segregation errors, which were monitored by sectoring assays. Chromosome loss errors (1:0) in these hsHec1S165E mutant cells were especially prominent compared with wild-type cells (strain WHL2003) or scHec1 null cells rescued by wild-type hsHec1 (strain WHL4003). Yeast cells without scNek2 (strain WHL6502) had a much higher incidence of chromosome segregation errors compared to cells rescued by wild-type hsHec1 or hsHec1S165E. NS, not significant.

| Yeast strain | Genotype | Total colony number | Chromosome segregation events | | | |
|---|---|---|---|---|---|---|
| | | | 1:0 | Significance versus weight | 2:0 | Significance versus weight |
| WHL2003[a] | scHEC1/scHEC1 scNek2/scNek2 | 10,021 | 2 (0.02%) | | 1 (0.01%) | |
| WHL4003 | Δschec1/Δschec1 hsHEC1/hsHEC1 scNek2/scNek2 | 10,483 | 2 (0.02%) | $X^2 = 0.00203$ (NS) | 2 (0.02%) | $X^2 = 0.290$ (NS) |
| WHL4001 | Δschec1/Δschec1 hsHEC(S165E)/hsHEC1(S165E) scNek2/scNek2 | 5,748 | 8 (0.14%) | $X^2 = 8.54$ (p = 0.0035) | 1 (0.02%) | $X^2 = 0.159$ (NS) |
| WHL6502 | scHEC1/scHEC1 ΔscNek2/ΔscNek2 | 6,770 | 502 (7.42%) | $X^2 = 756$ (p < 0.0001) | 4 (0.06%) | $X^2 = 1.83$ (NS) |

[a]Adapted from Zheng L. et al. Mol. Cell. Biol. (1999) 19: 5417-5428

EXAMPLE II

Interaction Between Hec1p and its Associated Protein, Hint-1

Figure 9A:
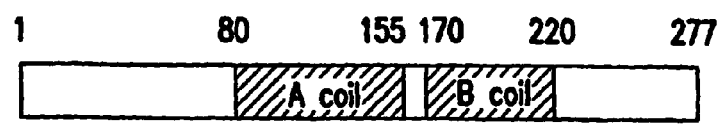
FIG. 9A-9B. Interaction between Hint1 and Hec1 by GST pull-down assay.
Figure 9B:
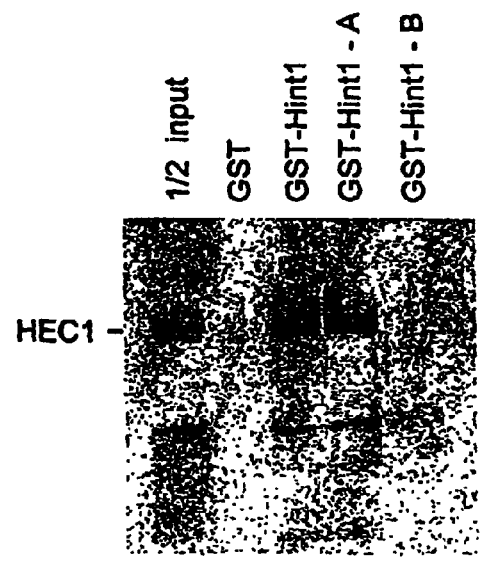

Using the yeast two-hybrid method, we have identified at least five known interacting proteins with Hec-1, including MSS1, SMC1, Nek2, p45 of the 26S proteosome and RB, and two novel proteins, 15A2 and 15A20. The 15A20 protein, later re-named as Hint1, has two coil-coiled domains at the middle of the protein. Using in vitro GST-pull-down assay, Hint1 binds to Hec-1 with its "A" coil-coiled domain (FIG. 9A-9B). Reciprocally, Hec1 binds to Hint1 with its first two coil-coiled domains.

Figure 10:
FIG. 10. Cell cycle-dependent interaction between Hec1 nd Hint1. T24 bladder carcinoma cells were first density-arrested at G1 (lane 2) and then released for re-entry into the cell cycle. At different time points after released from density arrest (indicated above the lanes), cells were collected and lysed. The clarified lysates were immunoprecipitated with mAb9G3 anti-Hec1 monoclonal antibodies (second panel from top) or anti-Hint1 antisera (bottom panel). Hec1 and Hint1 were co-immunoprecipitated at M phases (third panel from top, lane 7). The top panel shows the synchronization of T24 cells, as indicated by Rb phosphorylation.

Expression of Hint1 was cell-cycle dependent with the highest level at the M phase, a pattern similar to Hec1. Hec1 was specifically co-immunoprecipitated with anti-Hint-1 antibodies at M phase but not during the interphase (FIG. 10). Hint-1 interacts with ZW10 at the kinetochore (Starr et al. "HZwint-1, a novel human kinetochore component that interacts with HZW10." *J. Cell Sci.* 113 (Pt 11):1939-50, 2000) during chromosome segregation. Moreover, Hint-1 appears to relocate at the kinetochore first and then ZW10, which helps recruit dynactin and dynein to the kinetochore. Since Hec1 is a kinetochore protein, it is likely that Hec1 recruits Hint1/Zw10 to the kinetochore to form an active kinetochore for the attachment of the spindle.

EXAMPLE III

Isolation of Small Molecules by Reverse Yeast Two-Hybrid Screening for Disrupting the Interaction Between Hec1 and Nek2

We have established a reverse yeast two-hybrid assay for screening molecules that disrupt the interaction between acid (5FOA) to fluoroorotidine monophosphate that in turn generates 5-fluorouridine monophosphate to inhibit growth (Boeke et al. "5-Fluoroorotic acid as a selective agent in yeast molecular genetics." *Methods Enzymol.* 1987; 154:164-75). Yeast cells will grow only in the presence of an inhibitor that disrupts the interaction of TetR/Hec1 and AD/Nek2 because no URA3 gene product is made.

This approach is suitable for high throughput screening. We have used this system to screen 40,000 chemicals from a 100,000 chemical library purchased from Nonosyn, Inc. (Menlo Park, Calif.). Thus far, eight small-molecule chemicals have been identified that are able to promote yeast growth at concentrations of about 10 μM. To further demonstrate that these molecules specifically inhibit the interaction between Hec1 and Nek2, we tested their respective abilities to disrupt the interaction of other protein pairs, including BRCA2 and Rad51. We found that these compounds are specific for disrupting the interaction between Hec1 and Nek2, at least in yeast. Based on these results, it is clear that this assay can be used to identify additional molecules that can be used to disrupt the interaction between Hec1 and Nek2. For example, it is likely that molecules sharing similar chemical structures to the above-described compounds can be identified using this exemplary assay.

Figure 12:
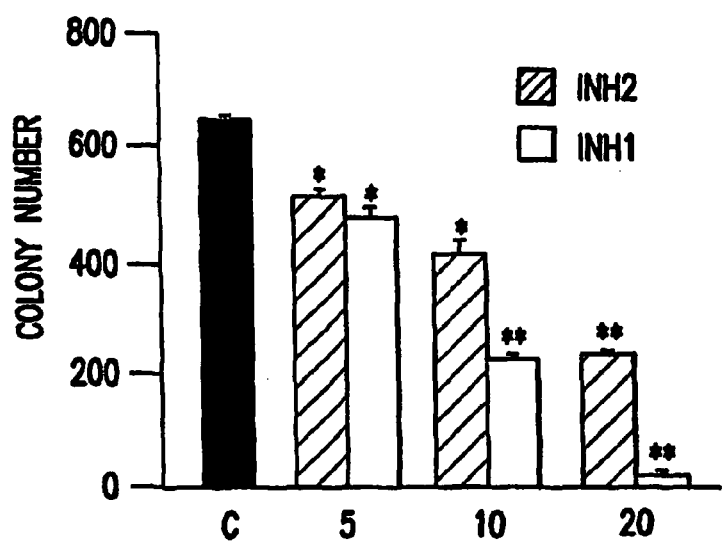
FIG. 12. Effects of INH1 and INH2 on colony formation of HeLa cells. Exponentially grown cells were seeded at 800 cells per 10-cm dish for 24 h and treated with indicated concentrations of INH1 (MW: 308.41; also referred to herein as IBT 13131; see FIG. 17), INH2 (MW 382.49; also referred to herein as IBT 14664; see FIG. 17), or control (DMSO less than 0.1%) for 12 days. The colonies were fixed and stained with methylene blue and counted. The values were averaged from a triplicate set of experiments, and error bars represent the SEM. Results that differed significantly from control are indicated: *, $p<0.05$; **, $p<0.01$.

To determine whether the identified compounds would have the same effect in mammalian cells, we used HeLa cells to test the effects of these compounds in a small-scale experiment. With a dose of 20 two of the original eight compounds showed significant activity in killing dividing cells. These two compounds were named INH1 and INH2 (INH1, MW: 308.41; also referred to herein as IBT 13131; see FIG. 16; INH2, MW 382.49; also referred to herein as IBT 14664; see FIG. 16). Interestingly, these two chemicals contain a core N-(4-phenylthiazol-2-yl)benzamide structure with additional groups on both sides of the benzene rings. The remaining six compounds that showed no activity did not share the same core structure. INH1 is smaller than INH2, and has a significant higher killing activity (FIG. 12) as measured by colony formation assays.

Figure 13A:
FIG. 13A-13B. INH disrupts the interaction between Hec1 and Nek2 in HeLa cells.
Figure 13B:
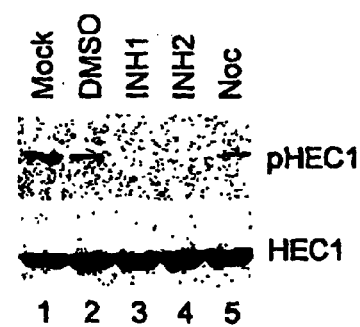

We performed a co-immunoprecipitation assay using cells treated with INH1 or INH2 to test whether these compounds disrupt the interaction between Hec1 and Nek2. As shown in FIG. 13A-13B, immunoprecipitation of anti-Hec1 antibodies co-precipitated very little or no Nek2 protein from cells treated with INH1 at 10 and 20 µM, whereas immunoprecipitation of Hec1 from cells treated with solvent (DMSO) brought down Nek2 (FIG. 13A). Similarly, we examined whether Nek2 phosphorylation of Hec1 is diminished in the cells treated with these drugs by Western blotting with anti-A349, which recognizes specifically the phosphorylated S165 of Hec1. Our observation suggests that the Nek2 phosphorylation of Hec1 was abolished in cells treated with 20 µM of INH1 and 2, but not in untreated or DMSO treated cells (FIG. 13B).

Our initial findings suggest that INH1 generated chromosome missegregations similar to that observed in Hec1 depleted cells, which eventually led to cell death, as indicated by FACS analysis (FIG. 14A-14B).

EXAMPLE IV

Testing the Efficacy of Hec1 Inhibitors in Cancer Cells with Different Genetic Backgrounds in Culture and in Nude Mice Cancer cells with different genetic backgrounds, especially with Rb or p53 deficiency, might have higher sensitivities toward the compounds that inhibit Hec1 activity. Because Rb has a positive function in chaperoning Hec1 function during M phase (Zheng et al. "Retinoblastoma protein enhances the fidelity of chromosome segregation mediated by hsHec1p." *Mol. Cell. Biol.* 20:3529-37, 2000), it is possible that a smaller amount of drug would be required to inactivate Hec1 in RB deficient cells. This can be tested by using pair-wise RB-proficient and RB-deficient isogenic cancer cell lines (Huang et al. "Suppression of the neoplastic phenotype by replacement of the RB gene in human cancer cells." *Science* 242:1563-1566, 1988); such cell lines include retinoblastoma WERI 27, osteosarcoma Saos2, breast cancer MB-MD-468, bladder carcinoma cells HT1376, and prostate cancer cell line DU145.

In experiments using Saos2 cells, we found that fewer than 5% of RB-reconstituted Saos2 cells (SR5) were killed when treated with 10 µM of INH1 but more than 50% of parental (RB-negative) Saos2 cells were killed under the same condition (FIG. 15). This result shows that there should be a good therapeutic window for treating RB-deficient tumors, which occur in a substantial number of patients.

The efficacy of Hec1-inhibitory small molecules can also be tested in nude mice bearing tumors. Xenograft nude mice are generated, using well-known approaches, e.g., by using the following RB-deficient tumor lines: retinoblastoma cell line Y79; breast cancer line MDA-MB468; prostate cancer cell line DU145; bladder carcinoma cell line 5637; and osteosarcoma cell line Saos2. For example, for each study, female athymic nude-nu (nude) mice (e.g., from Harlan Sprague Dawley, Inc.) weighing approximately 20-25 g are implanted s.c. (subcutaneously) by inoculation with tumor cell suspensions. When tumors reach approximately 5×5 mm (about ten to fourteen days after inoculation), animals are pair-matched into treatment and control groups. Each group contains, e.g., five tumor-bearing mice, each of which is followed individually throughout the experiment. The administration of drugs or vehicle can begin the day the animals are pair-matched (Day 1), or any other suitable day.

Maximum Tolerance Dose (MTD) can be determined for Hec1-inhibitory compounds, e.g., as follows. The dose to be tested can start, e.g., from 25 to 50 mg/kg, which is in the range comparable with β-Lapachone (Li et al. 1999 "Potent inhibition of tumor survival in vivo by beta-lapachone plus taxol: combining drugs imposes different artificial checkpoints." *Proc. Natl. Acad. Sci. U.S.A.* 96(23):13369-74, 1999), a drug shown to be effective at dosages between 25 and 50 mg/kg. The toxicity of the compounds can be evaluated by body weight gain and general appearance of the mice. After determining the MTD, ½, ¼, and ⅛ dosages of the compounds can be administered to the xenograft mice intraperitoneally in order to measure tumor growth inhibition (TGI) and tumor growth delay (TGD) for about 30 days. A commonly used cancer drug, e.g., Taxotere, can be used as a positive control, e.g., at the dose of 1 mg/kg. Five nude mice can be used for each dose group. Mice are treated, e.g., for a total 10 cycles with a 1-day break between each cycle. Mice are weighed regularly, e.g., twice weekly, and tumor measurements are taken regularly, e.g., twice weekly, starting on Day 1. These tumor measurements can be converted to mg tumor weight by a well-known formula, (W2×L)/2. The experiments are terminated at a specific endpoint, e.g., when control tumors reach a weight of 1 gram. Upon termination, all mice are weighed, sacrificed, and their tumors excised. The tumors are weighed, and the mean tumor weight per group is calculated. In these models, the change in mean treated tumor weight/the change in mean control tumor weight×100% (ΔT/ΔC) is subtracted from 100% to calculate the TGI for each group. Some drugs may cause tumor regression in the human tumor xenograft models. With these chemicals, the final weight of a given tumor is subtracted from its own weight at the start of treatment on Day 1. This difference divided by the initial tumor weight is the percent regression, and average percent tumor regression will be calculated. If the tumor completely disappears in a mouse, this is considered as complete regression. If desired, mice with partial or total tumor regressions can be kept alive past the planned termination date to determine the effect of the treatment on survival. The final size of each group can be defined statistical estimations based on preliminary pilot experiments, as will be understood by the skilled artisan. Beneficial effects can also be evaluated by comparing the mortality rates in control and treatment groups.

Incorporation by Reference

Throughout this application, various publications, patents, and/or patent applications are referenced in order to more fully describe the state of the art to which this invention pertains. The disclosures of these publications, patents, and/or patent applications are herein incorporated by reference in their entireties, and for the subject matter for which they are specifically referenced in the same or a prior sentence, to the same extent as if each independent publication, patent, and/or patent application was specifically and individually indicated to be incorporated by reference. Nothing herein is to be construed as an admission that the invention is not entitled to antedate such disclosure by virtue of prior invention.

OTHER EMBODIMENTS

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating an Rb-deficient cancer, comprising administering to a subject with Rb-deficient cancer a compound selected from the group consisting of N-[4-(2,4-dimethylphenyl)thiazol-2-yl)benzamine, IBT13131, having the formula:

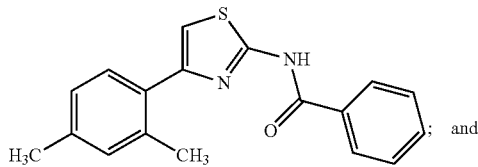

; and

N-[4-(2,4,6-trimethylphenyl)thiazol-2-yl)-2,4-dimethoxybenzamine, IBT14664, having the formula:

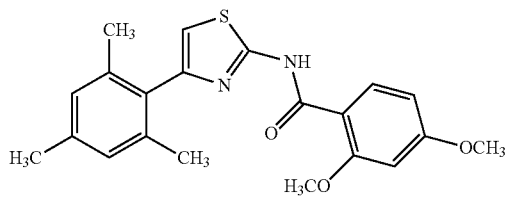

thereby inhibiting the interaction between a Hec1 protein and at least one further protein.

2. The method of claim 1, wherein the Rb-deficient cancer is selected from the group consisting of: bladder carcinoma, breast carcinoma, cervical carcinoma, osteosarcoma, and prostate carcinoma.

3. The method of claim 1, wherein the Rb-deficient cancer is retinoblastoma.

4. A method of identifying a compound that reduces an interaction between Hec1 protein and Hint1 protein, comprising:
   a) contacting Hec1 protein with Hint1 protein in the relative absence of the compound;
   b) contacting Hec1 protein with Hint1 protein in the relative presence of the compound; and
   c) determining the relative amount of interaction between the Hec1 protein and the Hint1 protein in a) and b);
   wherein if the relative presence of the compound causes less interaction than the relative absence of the compound, the compound is identified as a compound that reduces an interaction between the Hec1 protein and Hint1 protein.

5. The method of claim 4, further comprising contacting Hec1 with Nek2 protein.

6. The method of claim 4, wherein the Hec1 protein is immobilized and the relative amount of interaction is determined by measurement of co-immobilization of the Hint1 protein.

7. The method of claim 4, wherein the Hint1 protein is immobilized and the relative amount of interaction is determined by measurement of co-immobilization of the Hec1 protein.

8. The method of claim 4, wherein b) and c) include immunoprecipitation of proteins.

9. The method of claim 4, wherein b) and c) include co-localization of labels specific for Hec1 protein and Hint1 protein.

* * * * *